(12) United States Patent
Kohle et al.

(10) Patent No.: US 12,626,792 B2
(45) Date of Patent: May 12, 2026

(54) HEALTHCARE NETWORK

(71) Applicant: Siemens Healthcare GmbH, Erlangen (DE)

(72) Inventors: Sven Kohle, Erlangen (DE); Michael Rusitska, Utternreuth (DE); Simon Allen-Raffl, West Chester, PA (US); Christian Tietjen, Fuerth (DE); Marcus Thaele, Fuerth (DE); Gerardo Hermosillo Valadez, West Chester, PA (US); Steffen Weichert, Hannover (DE); Johannes Baeck, Hannover (DE); Felix Nensa, Essen (DE); Saulius Archipovas, Bremen (DE); Felix Ritter, Bremen (DE)

(73) Assignee: SIEMENS HEALTHINEERS AG, Forccheim (DE)

( * ) Notice: Subject to any disclaimer, the term of this patent is extended or adjusted under 35 U.S.C. 154(b) by 453 days.

(21) Appl. No.: 17/950,398

(22) Filed: Sep. 22, 2022

(65) Prior Publication Data

US 2023/0012685 A1     Jan. 19, 2023

Related U.S. Application Data

(63) Continuation of application No. 16/294,997, filed on Mar. 7, 2019, now Pat. No. 11,482,309.

(30) Foreign Application Priority Data

Mar. 7, 2018     (EP) .................................... 18160372

(51) Int. Cl.
      *G16H 50/20*          (2018.01)
      *G16H 10/60*          (2018.01)
                (Continued)

(52) U.S. Cl.
      CPC ............. *G16H 10/60* (2018.01); *G16H 15/00* (2018.01); *G16H 30/20* (2018.01); *G16H 50/20* (2018.01);
                (Continued)

(58) Field of Classification Search
      CPC ........ G16H 10/60; G16H 15/00; G16H 30/20; G16H 50/20; G16H 80/00; G06Q 10/10; G06Q 40/08
      See application file for complete search history.

(56) References Cited

U.S. PATENT DOCUMENTS

2002/0091687 A1     7/2002  Eglington
2002/0107824 A1     8/2002  Ahmed
                (Continued)

FOREIGN PATENT DOCUMENTS

CN          1398376  A     2/2003
CN        101228543  A     7/2008
                (Continued)

OTHER PUBLICATIONS

Liew, Charlene, The Future of Radiology Augmented with Artificial Intelligence: A Strategy for Success, European Journal of Radiology, vol. 102, 2018, pp. 152-156 (Year: 2018).*
                (Continued)

*Primary Examiner* — Matthew L Hamilton
(74) *Attorney, Agent, or Firm* — Harness, Dickey & Pierce, P.L.C.

(57)     ABSTRACT

A system is used to control operation of a user device. An association between a medical condition and one or more decision trees is maintained. Each decision tree includes nodes organised in a tree structure originating at a root node and terminating at leaf nodes via branch nodes. The nodes are linked to each other via outputs and each output causes the system to differently control operation of the user device.
                (Continued)

Responsive to receiving medical information associated with the patient, using the association, a decision tree is identified. For the root node of the identified decision tree: a first node is selected, responsive to receiving data indicative of a first output regarding the root node; the user device is caused to retrieve medical information from one or more data sources based on the first node; and the retrieved medical information is caused to be displayed on the user device.

23 Claims, 16 Drawing Sheets

(51) Int. Cl.

| | |
|---|---|
| *G16H 15/00* | (2018.01) |
| *G16H 30/20* | (2018.01) |
| *G16H 80/00* | (2018.01) |
| *G06Q 10/10* | (2023.01) |
| *G06Q 40/08* | (2012.01) |

(52) U.S. Cl.
CPC ............. *G16H 80/00* (2018.01); *G06Q 10/10* (2013.01); *G06Q 40/08* (2013.01)

(56) References Cited

U.S. PATENT DOCUMENTS

| | | | |
|---|---|---|---|
| 2003/0028401 A1 | 2/2003 | Kaufman et al. | |
| 2004/0044546 A1 | 3/2004 | Moore | |
| 2006/0116908 A1 | 6/2006 | Dew et al. | |
| 2009/0062623 A1 | 3/2009 | Cohen et al. | |
| 2009/0094063 A1 | 4/2009 | Ennett | |
| 2010/0080427 A1* | 4/2010 | Yeluri | G16H 30/20 382/128 |
| 2011/0029322 A1 | 2/2011 | Hindo et al. | |
| 2011/0046979 A1 | 2/2011 | Tulipano et al. | |
| 2012/0129139 A1 | 5/2012 | Partovi | |
| 2013/0129198 A1* | 5/2013 | Sherman | G16H 30/20 382/159 |
| 2014/0025393 A1 | 1/2014 | Wang et al. | |
| 2014/0143719 A1* | 5/2014 | Arazi | G16H 30/20 715/810 |
| 2014/0185888 A1 | 7/2014 | Kelm et al. | |
| 2014/0278492 A1 | 9/2014 | Silver et al. | |
| 2014/0324469 A1 | 10/2014 | Reiner | |
| 2014/0365239 A1 | 12/2014 | Sadeghi | |
| 2015/0149212 A1 | 5/2015 | Rolia et al. | |
| 2016/0004236 A1 | 1/2016 | Stubbs | |
| 2016/0203281 A1 | 7/2016 | Zalis et al. | |
| 2019/0015080 A1* | 1/2019 | Kreuzer | G16H 30/20 |
| 2019/0027243 A1 | 1/2019 | Amthor et al. | |
| 2019/0043441 A1* | 2/2019 | Reicher | H04N 9/73 |
| 2019/0180862 A1 | 6/2019 | Wisser et al. | |
| 2021/0065899 A1* | 3/2021 | Aladahalli | G16H 30/40 |

FOREIGN PATENT DOCUMENTS

| | | | |
|---|---|---|---|
| CN | 101400298 A | 4/2009 | |
| CN | 102016859 A | 4/2011 | |
| CN | 104123395 A | 10/2014 | |
| CN | 104254857 A | 12/2014 | |
| CN | 105210065 A | 12/2015 | |
| JP | 2001166803 A | 6/2001 | |
| JP | 2009061176 A | 3/2009 | |
| WO | WO-2003107250 A2 | 12/2003 | |
| WO | WO 2014197669 A1 | 12/2014 | |
| WO | WO-2018002025 A1 | 1/2018 | |

OTHER PUBLICATIONS

Quellec Gwenole et al:"Multimedia medical case retrieval using decision trees", Proceedings of the 29th Annual International Conference of the IEEE EMBS Cité Internationale, Lyon, France Aug. 23-26, 2007. Oct. 22, 2007.

Ni Jiayuan er al:"Design of Diabetes Diagnosis Expert System Based on Decision Tree And Object-oriented Technology", Journal of Suzhou University of Science and Technology (Natural Science), No. 01, Mar. 15, 2016.

European Summons to Attend Oral Hearing dated Apr. 11, 2019.

European Communication mailed Aug. 22, 2019.

European Office Action dated Feb. 16, 2021 issued in corresponding European Application No. 20 156 811.0-1126.

European Search Report for European Application No. 18160372 dated Jul. 26, 2018.

Extended European Search Report dated May 28, 2020.

* cited by examiner

FIG 5

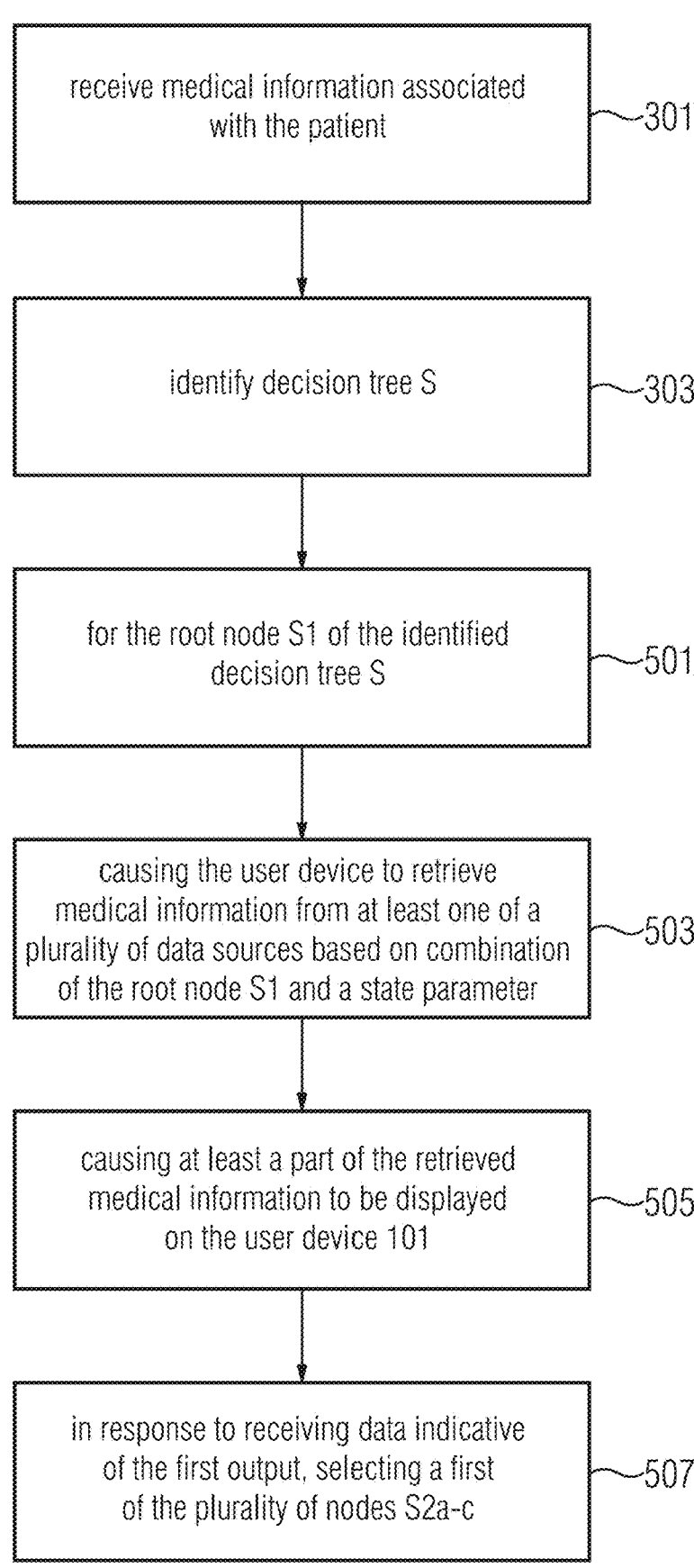

receive medical information associated with the patient ~301 identify decision tree S ~303 for the root node S1 of the identified decision tree S ~501 causing the user device to retrieve medical information from at least one of a plurality of data sources based on combination of the root node S1 and a state parameter ~503 causing at least a part of the retrieved medical information to be displayed on the user device 101 ~505 in response to receiving data indicative of the first output, selecting a first of the plurality of nodes S2a-c ~507

FIG 6

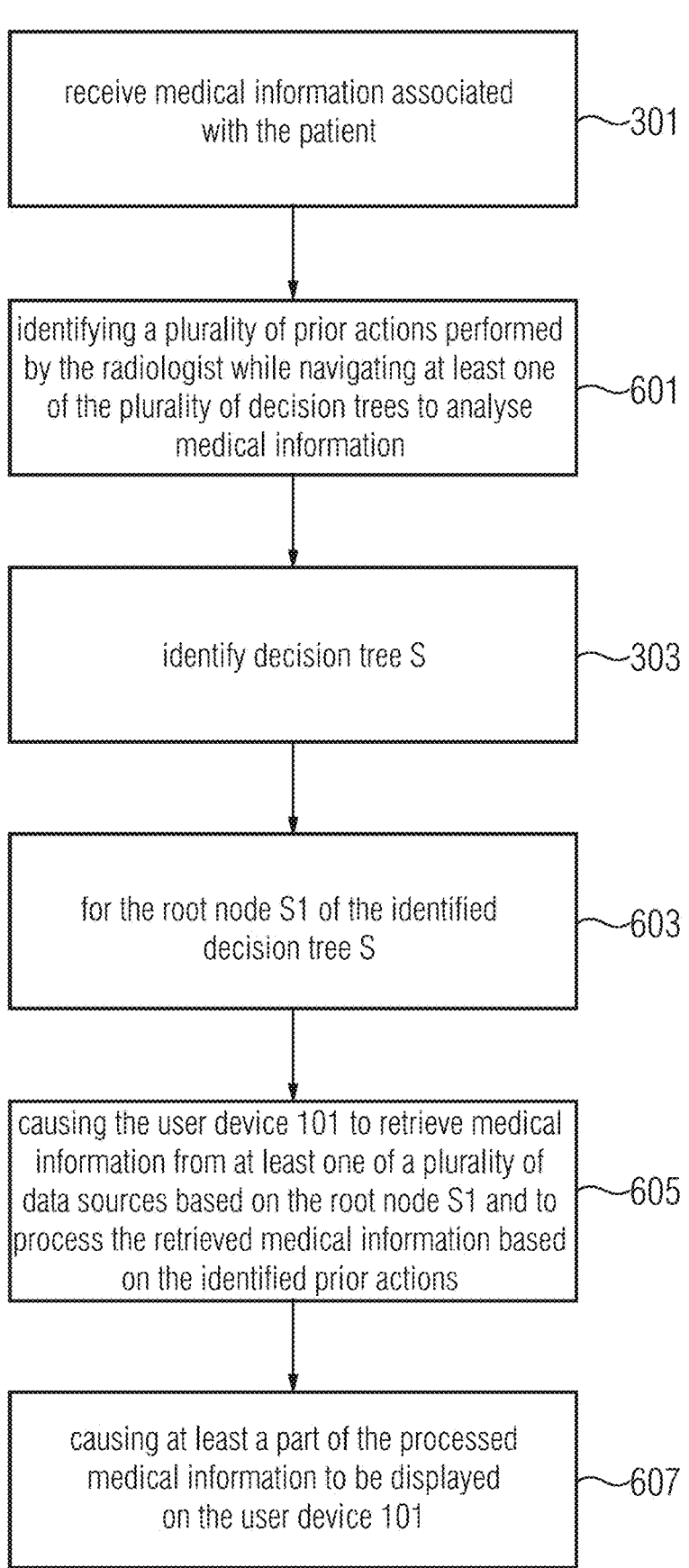

receive medical information associated
with the patient                                    ~301 identifying a plurality of prior actions performed
by the radiologist while navigating at least one
of the plurality of decision trees to analyse
medical information                                  ~601 identify decision tree S                            ~303 for the root node S1 of the identified
decision tree S                                     ~603 causing the user device 101 to retrieve medical
information from at least one of a plurality of
data sources based on the root node S1 and to
process the retrieved medical information based
on the identified prior actions                     ~605 causing at least a part of the processed
medical information to be displayed
on the user device 101                              ~607

700

Patient Name A
Birthday

Patient Name A
Birthday

Figure 13:
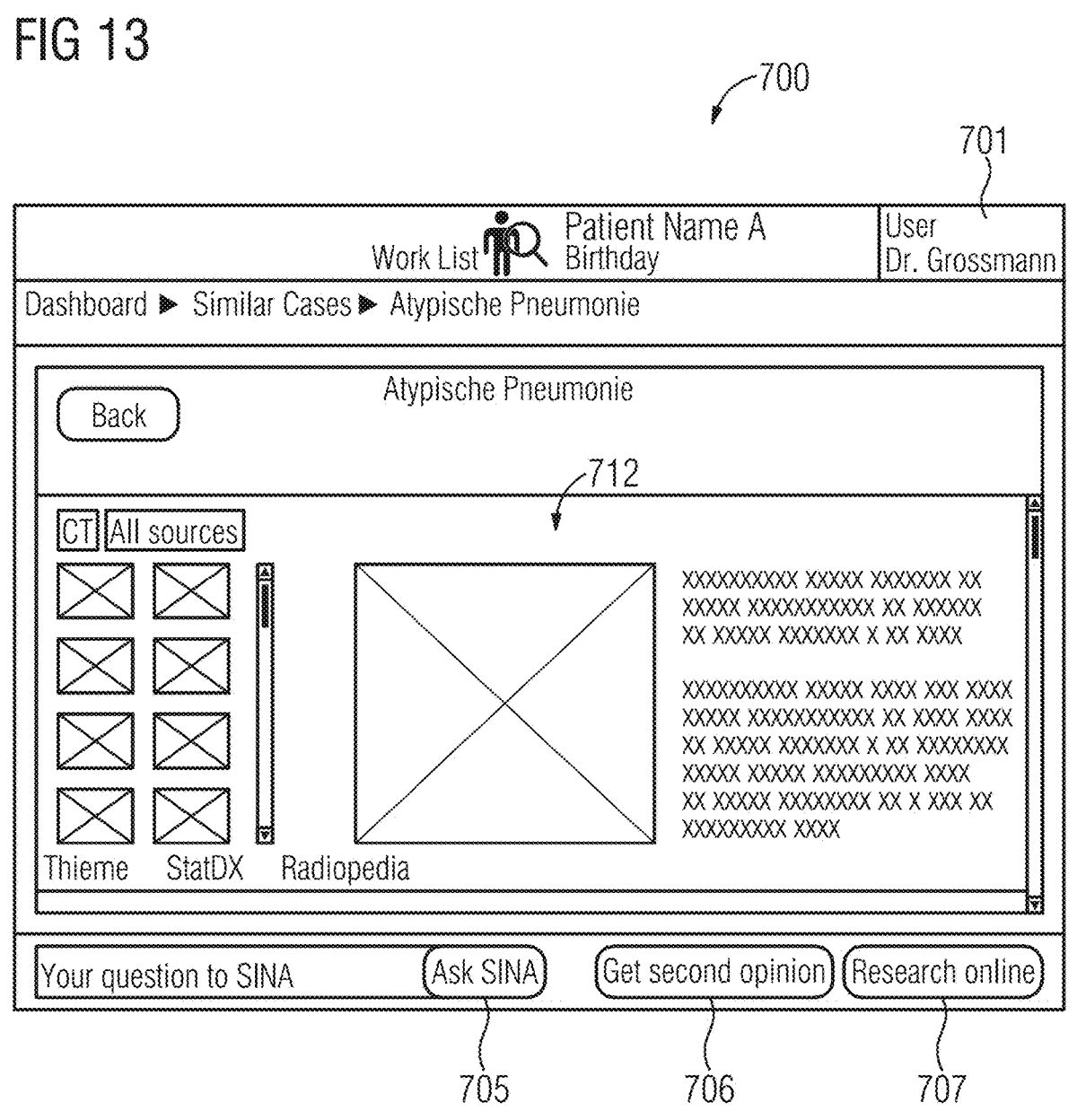

Work List  Patient Name A  Birthday    User  Dr. Grossmann

Dashboard ▶ Similar Cases ▶ Atypische Pneumonie

Atypische Pneumonie

Back

712

CT | All sources

Thieme    StatDX    Radiopedia

XXXXXXXXX XXXX XXXXXX XX
XXXX XXXXXXXXXX XX XXXXX
XX XXXXX XXXXXX X XX XXXX

XXXXXXXXX XXXX XXXX XXX XXXX
XXXX XXXXXXXXXX XX XXXX XXXX
XX XXXXX XXXXXX X XX XXXXXXX
XXXX XXXX XXXXXXXX XXXX
XX XXXXX XXXXXXX XX X XXX XX
XXXXXXXXX XXXX

Your question to SINA    Ask SINA    Get second opinion    Research online 705    706    707

Figure 15:
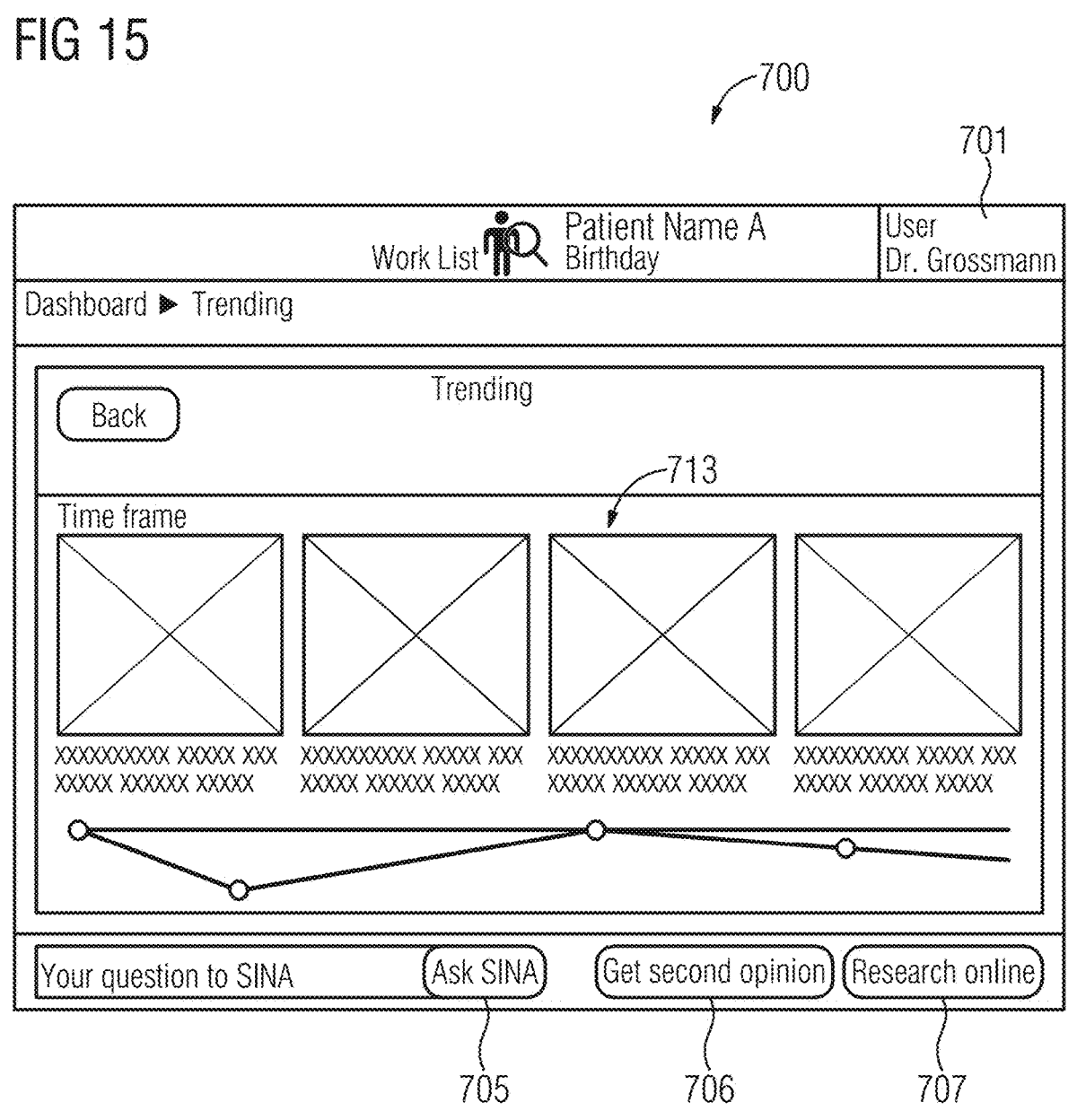

Work List  Patient Name A  Birthday          User  Dr. Grossmann

Dashboard ▶ Trending

Trending

Back

713

Time frame

XXXXXXXXX XXXXX XXX   XXXXXXXXX XXXXX XXX   XXXXXXXXX XXXXX XXX   XXXXXXXXX XXXXX XXX
XXXX XXXXX XXXXX       XXXX XXXXX XXXXX       XXXX XXXXX XXXXX       XXXX XXXXX XXXXX

Your question to SINA          Ask SINA          Get second opinion          Research online 705          706          707

HEALTHCARE NETWORK

PRIORITY STATEMENT

The present application is a continuation of U.S. application Ser. No. 16/294,997, filed on Mar. 7, 2019, and hereby claims priority under 35 U.S.C. § 119 to European patent application number EP18160372.1 filed Mar. 7, 2018, the entire contents of each of which are hereby incorporated herein by reference.

FIELD

Embodiments of the invention generally relate, but not exclusively, to systems, methods and computer programs usable in controlling operation of a user device configured for use by a radiologist when analysing medical information associated with a patient.

BACKGROUND

A healthcare network enables accumulation and/or provisioning of healthcare, clinical and/or medical data. The healthcare network comprises a plurality of systems including devices and software applications. The devices may include medical devices (e.g. an ultrasound system or other imaging modalities for Computed Tomography, Nuclear Magnetic Resonance Imaging or the like), user devices for use by medical professionals and patients, specialist user terminals (e.g. nurse call system), servers and medical data sources. Software applications operate on, or in conjunction with or are accessible via, the devices, and may include communication applications that facilitate communication between devices on the healthcare network, medical applications configured to process medical information, applications configured to manage patient information, applications for managing knowledge in a healthcare environment, and applications configured to manage medical records.

Typically, a healthcare network comprises several disparate data sources, which are rarely integrated so as to operate homogeneously. A radiologist, when analysing medical information associated with a patient, may need healthcare information from different data sources at different stages of the analysis. In addition, healthcare professionals from different disciplines may need different healthcare data for their analysis. For example, different members of a multidisciplinary group of healthcare professionals that reviews ongoing cases may need access to different healthcare data. However, as the data sources are not integrated, radiologists have to manually retrieve medical information from relevant data sources at every stage of their analysis.

Therefore, it is desirable to provide a homogeneous healthcare environment in which information from disparate data sources can be seamlessly accessed and presented to a radiologist. In addition, it is desirable to automatically retrieve, adapt and/or update information from disparate data sources via a user interface based on a frame of reference. It is also desirable to automatically select and update functions provisioned via the user interface to enable a radiologist to analyse the presented medical information.

SUMMARY

In a first embodiment, there is provided a system operable to control operation of a user device, the user device being configured for use by a radiologist when analysing medical information associated with a patient, the system comprising at least one processor and at least one memory including computer program code, the at least one memory and the computer program code configured to, with the at least one processor, cause the system at least to perform at least:

maintaining, in a database, an association between a medical condition and at least one of a plurality of decision trees, each decision tree comprising a plurality of nodes organised in a tree structure originating at a root node and terminating at a plurality of leaf nodes via a plurality of branch nodes, wherein the root node and each of the branch nodes have a plurality of outputs, each of the plurality of outputs links a node of the plurality of nodes to a further node of the plurality of nodes and wherein each output causes the system to differently control operation of the user device;

in response to receiving medical information associated with the patient, identifying, based on the association, a decision tree from the plurality of decision trees; and for the root node of the identified decision tree, performing a process comprising:

in response to receiving data indicative of a first of a plurality of outputs in connection with the root node, selecting a first of the plurality of nodes;

causing the user device to retrieve medical information from at least one of a plurality of data sources based on the first node; and causing at least a part of the retrieved medical information to be displayed on the user device.

In a second embodiment, there is provided a method of controlling operation of a user device, the user device being configured for use by a radiologist when analysing medical information associated with a patient, the method comprising:

maintaining, in a database, an association between a medical condition and at least one of a plurality of decision trees, each decision tree comprising a plurality of nodes organised in a tree structure originating at a root node and terminating at a plurality of leaf nodes via a plurality of branch nodes, wherein the root node and each of the branch nodes have a plurality of outputs, each of the plurality of outputs links a node of the plurality of nodes to a further node of the plurality of nodes and wherein each output causes operation of the user device to be differently controlled;

in response to receiving medical information associated with the patient, identifying, based on the association, a decision tree from the plurality of decision trees; and for the root node of the identified decision tree, performing a process comprising:

in response to receiving data indicative of a first of a plurality of outputs in connection with the root node, selecting a first of the plurality of nodes;

causing the user device to retrieve medical information from at least one of a plurality of data sources based on the first node; and causing at least a part of the retrieved medical information to be displayed on the user device.

In a third embodiment, there is provided a computer program comprising a set of instructions, which, when executed by a computerised device, cause the computerised device to perform a method of controlling operation of a user device, the user device being configured for use by a radiologist when analysing medical information associated with a patient, the method comprising, at the computerised device:

maintaining, in a database, an association between a medical condition and at least one of a plurality of decision trees, each decision tree comprising a plurality of nodes organised in a tree structure originating at a root node and terminating at a plurality of leaf nodes via a plurality of branch nodes, wherein the root node and each of the branch nodes have a plurality of outputs, each of the plurality of outputs links a node of the plurality of nodes to a further node of the plurality of nodes and wherein each output causes operation of the user device to be differently controlled;

in response to receiving medical information associated with the patient, identifying, based on the association, a decision tree from the plurality of decision trees; and for the root node of the identified decision tree, performing a process comprising:

in response to receiving data indicative of a first of a plurality of outputs in connection with the root node, selecting a first of the plurality of nodes;

causing the user device to retrieve medical information from at least one of a plurality of data sources based on the first node; and causing at least a part of the retrieved medical information to be displayed on the user device.

In a fourth embodiment, there is provided a system operable to control operation of a user device, the user device being configured for use by a radiologist when analysing medical information associated with a patient, the system comprising at least one processor and at least one memory including computer program code, the at least one memory and the computer program code configured to, with the at least one processor, cause the system at least to perform:

maintaining, in a database, an association between a medical condition and at least one of a plurality of decision trees, each decision tree comprising a plurality of nodes organised in a tree structure originating at a root node and terminating at a plurality of leaf nodes via a plurality of branch nodes, wherein the root node and each of the branch nodes have a plurality of outputs, each of the plurality of outputs links a node of the plurality of nodes to a further node of the plurality of nodes and wherein each output causes the system to differently control operation of the user device;

in response to receiving medical information associated with the patient, identifying, based on the association, a decision tree from the plurality of decision trees; and for the root node of the identified decision tree, performing a process comprising:

causing the user device to retrieve medical information from at least one of a plurality of data sources based on a combination of the root node and a state parameter, the state parameter being indicative of one of different stages associated with a determination regarding a first output in connection with the root node;

causing at least a part of the retrieved medical information to be displayed on the user device; and in response to receiving data indicative of the first output, selecting a first of the plurality of nodes.

In a fifth embodiment, there is provided a method of controlling operation of a user device, the user device being configured for use by a radiologist when analysing medical information associated with a patient, the method comprising:

maintaining, in a database, an association between a medical condition and at least one of a plurality of decision trees, each decision tree comprising a plurality of nodes organised in a tree structure originating at a root node and terminating at a plurality of leaf nodes via a plurality of branch nodes, wherein the root node and each of the branch nodes have a plurality of outputs, each of the plurality of outputs links a node of the plurality of nodes to a further node of the plurality of nodes and wherein each output causes operation of the user device to be differently controlled;

in response to receiving medical information associated with the patient, identifying, based on the association, a decision tree from the plurality of decision trees; and for the root node of the identified decision tree, performing a process comprising:

causing the user device to retrieve medical information from at least one of a plurality of data sources based on a combination of the root node and a state parameter, the state parameter being indicative of one of different stages associated with a determination regarding a first output in connection with the root node;

causing at least a part of the retrieved medical information to be displayed on the user device; and in response to receiving data indicative of the first output, selecting a first of the plurality of nodes.

In a sixth embodiment, there is provided a computer program comprising a set of instructions, which, when executed by a computerised device, cause the computerised device to perform a method of controlling operation of a user device, the user device being configured for use by a radiologist when analysing medical information associated with a patient, the method comprising, at the computerised device:

maintaining, in a database, an association between a medical condition and at least one of a plurality of decision trees, each decision tree comprising a plurality of nodes organised in a tree structure originating at a root node and terminating at a plurality of leaf nodes via a plurality of branch nodes, wherein the root node and each of the branch nodes have a plurality of outputs, each of the plurality of outputs links a node of the plurality of nodes to a further node of the plurality of nodes and wherein each output causes operation of the user device to be differently controlled;

in response to receiving medical information associated with the patient, identifying, based on the association, a decision tree from the plurality of decision trees; and for the root node of the identified decision tree, performing a process comprising:

causing the user device to retrieve medical information from at least one of a plurality of data sources based on a combination of the root node and a state parameter, the state parameter being indicative of one of different stages associated with a determination regarding a first output in connection with the root node;

causing at least a part of the retrieved medical information to be displayed on the user device; and in response to receiving data indicative of the first output, selecting a first of the plurality of nodes.

In a seventh embodiment, there is provided a system operable to control operation of a user device, the user device being configured for use by a radiologist when analysing medical information associated with a patient, the system comprising at least one processor and at least one memory including computer program code, the at least one memory and the computer program code configured to, with the at least one processor, cause the system at least to perform:

maintaining, in a database, an association between a medical condition and at least one of a plurality of decision trees, each decision tree comprising a plurality of nodes organised in a tree structure originating at a root node and terminating at a plurality of leaf nodes via a plurality of branch nodes, wherein the root node and each of the branch nodes have a plurality of outputs, each of the plurality of outputs links a node of the plurality of nodes to a further node of the plurality of nodes and wherein each output causes the system to differently control operation of the user device;

identifying a plurality of prior actions performed by the radiologist while navigating at least one of the plurality of decision trees to analyse medical information;

in response to receiving medical information associated with the patient, identifying, based on the association, a decision tree from the plurality of decision trees; and for the root node of the identified decision tree, performing a process comprising:

causing the user device to retrieve medical information from at least one of a plurality of data sources based on the root node and to process the retrieved medical information based on the identified prior actions; and causing at least a part of the processed medical information to be displayed on the user device.

In an eighth embodiment, there is provided a method of controlling operation of a user device, the user device being configured for use by a radiologist when analysing medical information associated with a patient, the method comprising:

maintaining, in a database, an association between a medical condition and at least one of a plurality of decision trees, each decision tree comprising a plurality of nodes organised in a tree structure originating at a root node and terminating at a plurality of leaf nodes via a plurality of branch nodes, wherein the root node and each of the branch nodes have a plurality of outputs, each of the plurality of outputs links a node of the plurality of nodes to a further node of the plurality of nodes and wherein each output causes operation of the user device to be differently controlled;

identifying a plurality of prior actions performed by the radiologist while navigating at least one of the plurality of decision trees to analyse medical information;

in response to receiving medical information associated with the patient, identifying, based on the association, a decision tree from the plurality of decision trees; and for the root node of the identified decision tree, performing a process comprising:

causing the user device to retrieve medical information from at least one of a plurality of data sources based on the root node and to process the retrieved medical information based on the identified prior actions; and causing at least a part of the processed medical information to be displayed on the user device.

In a ninth embodiment, there is provided a computer program comprising a set of instructions, which, when executed by a computerised device, cause the computerised device to perform a method of controlling operation of a user device, the user device being configured for use by a radiologist when analysing medical information associated with a patient, the method comprising, at the computerised device:

maintaining, in a database, an association between a medical condition and at least one of a plurality of decision trees, each decision tree comprising a plurality of nodes organised in a tree structure originating at a root node and terminating at a plurality of leaf nodes via a plurality of branch nodes, wherein the root node and each of the branch nodes have a plurality of outputs, each of the plurality of outputs links a node of the plurality of nodes to a further node of the plurality of nodes and wherein each output causes operation of the user device to be differently controlled;

identifying a plurality of prior actions performed by the radiologist while navigating at least one of the plurality of decision trees to analyse medical information;

in response to receiving medical information associated with the patient, identifying, based on the association, a decision tree from the plurality of decision trees; and for the root node of the identified decision tree, performing a process comprising:

causing the user device to retrieve medical information from at least one of a plurality of data sources based on the root node and to process the retrieved medical information based on the identified prior actions; and causing at least a part of the processed medical information to be displayed on the user device.

BRIEF DESCRIPTION OF THE DRAWINGS

FIG. 5 shows a flow diagram depicting an example of processing data in accordance with embodiments;

FIG. 6 shows a flow diagram depicting an example of processing data in accordance with embodiments; and FIGS. 7-16 present examples of the interface shown in accordance with embodiments.

DETAILED DESCRIPTION OF EXAMPLE EMBODIMENTS

Figure 1:
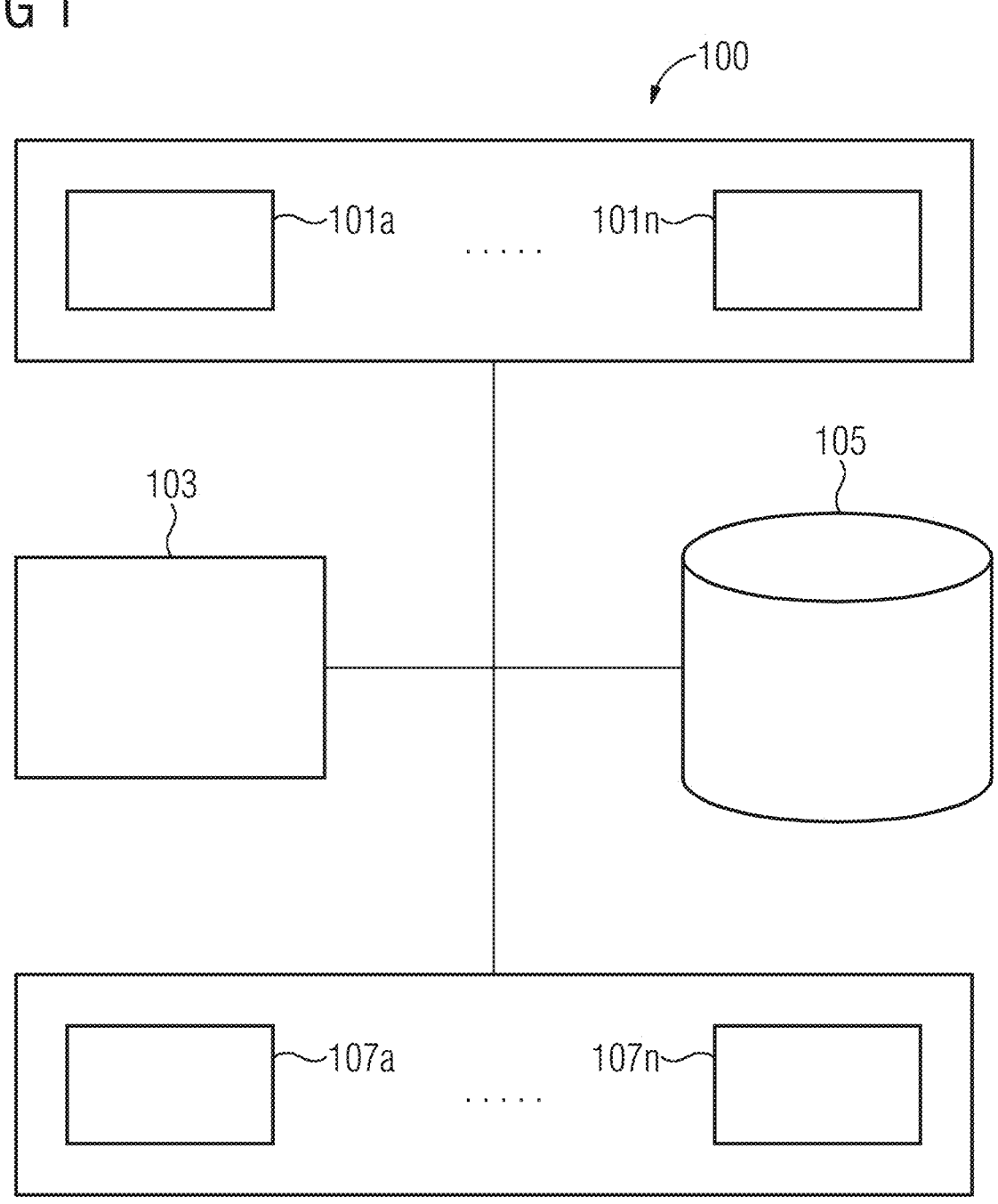
FIG. 1 shows a schematic block diagram of an example of a healthcare network in accordance with embodiments.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Most of the aforementioned components, in particular the identification unit, can be implemented in full or in part in the form of software modules in a processor of a suitable control device or of a processing system. An implementation largely in software has the advantage that even control devices and/or processing systems already in use can be easily upgraded by a software update in order to work in the manner according to at least one embodiment of the invention.

In a first embodiment, there is provided a system operable to control operation of a user device, the user device being configured for use by a radiologist when analysing medical information associated with a patient, the system comprising at least one processor and at least one memory including computer program code, the at least one memory and the computer program code configured to, with the at least one processor, cause the system at least to perform at least:

maintaining, in a database, an association between a medical condition and at least one of a plurality of decision trees, each decision tree comprising a plurality of nodes organised in a tree structure originating at a root node and terminating at a plurality of leaf nodes via a plurality of branch nodes, wherein the root node and each of the branch nodes have a plurality of outputs, each of the plurality of outputs links a node of the plurality of nodes to a further node of the plurality of nodes and wherein each output causes the system to differently control operation of the user device;

in response to receiving medical information associated with the patient, identifying, based on the association, a decision tree from the plurality of decision trees; and for the root node of the identified decision tree, performing a process comprising:

in response to receiving data indicative of a first of a plurality of outputs in connection with the root node, selecting a first of the plurality of nodes;

causing the user device to retrieve medical information from at least one of a plurality of data sources based on the first node; and causing at least a part of the retrieved medical information to be displayed on the user device.

User devices may comprise advanced visualization stations with a plurality of high resolution display screens, single computers, mobile devices like smartphones or tablets or the like. The data sources are medical data sources which may comprise a mix of disparate proprietary and off-the-shelf data sources. The data sources may, for example, include a picture archiving and communication system (PACS), an electronic medical records (EMR), an emergency care summary (ECS), a key information summary (KIS), an electronic patient record (EPR), a personal health record (PHR) and an expert system like online textbooks or cockpits, e.g. Thieme eRef, Radiopedia, an anatomical atlas, reference databases with proven diagnoses for similar cases or the like.

The medical information (also referred to as medical data) comprises clinical data (also referred to as clinical information) and/or healthcare data (also referred to as healthcare information). Clinical information comprises data collected during the course of ongoing patient care, e.g. laboratory test results and/or medical images acquired using at least one of a plurality of medical imaging modalities, e.g. image studies produced using Computed Tomography, Nuclear Magnetic Resonance, Positron-Emission-Tomography, X-Ray, Ultrasound or the like and/or as part of a formal clinical trial program, such as drug testing program. Clinical data may comprise: electronic health records of one or more patients, patient/disease registries indicative of data relating to chronic conditions such as Alzheimer's, clinical trials data, data for use in, for example, clinical or statistical decision support systems and/or anonymised patient medical records for, for example, use by a population health management system. Healthcare data may comprise administrative, regulatory and R&D (research and development) data, guidelines and/or legal regulations.

The radiologist (or another healthcare professional) analyses the medical information relevant for and/or related to one patient by reviewing the relevant inputs, such as symptoms and/or patient history, in order to take relevant steps regarding prevention, diagnosis, therapy and/or follow-up care. With other words, the radiologist's analysis may comprise deducing medical findings from medical image data and/or laboratory test results related to the patient. The system maintains and stores the association between a medical condition and at least one of a plurality of decision trees.

Therefore, the system advantageously integrates disparate data sources based on the information required by radiologists. The system may repeat the above process for each of the nodes successive to the first node of the identified decision tree, and thereby enable the radiologist (or another healthcare professional) to navigate the identified decision tree from the root node to the leaf nodes. Therefore, the system presents relevant medical information relevant for every node of the identified decision tree. The relevant medical information includes information required as input by a radiologist (or another healthcare professional) to navigate from a current node to a successive node. For example, the radiologist (or another healthcare professional) may require data indicative of age of a patient suspected with pneumonia because if the patient is less than three months old than they may require a full sepsis work-up, which may not be required for other patients.

The user interface or interface may be physically integrated with the user device or remote or separate from the user device. However, user device and user interface are connected to enable data transfer. The user interface is adapted to enable interaction of the user with the system. The user interface may be embodied in the form of a display screen which is connected with an input measure, e.g. a touchscreen, a mouse controller, a microphone for speech control or the like.

The system may additionally identify one or more of a plurality of functions usable for processing the retrieved medical information based on a combination of the first output and data indicative of the retrieved medical information. The one or more functions may preferably comprise image manipulation and/or evaluation measures/steps/actions typically used for deducing medical findings from medical images, for example, a function to measure size, volume and/or diameter/extent of a lesion, a function to measure distance of a lesion to a predefined landmark/organ, a function for certain color mapping, for zooming, for panning or fading out parts of the contained image information, for comparing medical images in part or in total, for identifying differences between medical images or the like. The system may cause the user device to provision the identified one or more of the plurality of functions to the radiologist (or another healthcare professional), whereby enabling processing of the retrieved medical information. The identified one or more of the plurality of functions may be presented via a user interface in conjunction with the relevant medical information, thereby reducing operational burden on a healthcare professional.

The system may maintain a state parameter indicative of a stage associated with a determination of a second output in connection with the first node, i.e. a current stage of analysis. The system may cause the user device to present at least part of the retrieved medical information based on the state parameter. The state parameter may, for example, be indicative of a stage intermediate between a current node and a successive node of the identified decision tree, and will be explained in more detail below.

The system, in response to receiving an input from the radiologist (or another healthcare professional), may cause the user device to present at least a part of the retrieved medical information based on a combination of the input and the state parameter. The input may, for example, comprise an interaction with the user interface, such as selection of a region of interest in a medical image, and/or further medical information, such as patient history. Therefore, the system dynamically adapts the information presented to the user based upon user activity.

The system may retrieve medical information based on: data indicative of the patient; data indicative of the radiologist (or another healthcare professional); data indicative of a medical condition; data indicative of one or more guidelines; data indicative of one or more legal regulations, e.g standards like BI-RADS (Breast Imaging Reporting and Data System), PI-RADS (Prostate Imaging Reporting and Data System) defined by the ACR (American College of Radiology); data acquired on the basis of monitoring of prior actions of the radiologist while navigating at least one of the plurality of decision trees to analyse medical information; data indicative of a customisation parameter; and/or data indicative of a user setting. A customization parameter may for example depend on the user knowledge or user experience, i.e. a senior radiologist does not need all possible functions or information presented to derive a reliable diagnosis, while a beginner would need more and/or more detailed assistance provided by the inventive system, User settings or a single user setting corresponds to a system setting defined and/or chosen by the user. Depending on a user setting the system may for example directly show comparable cases when a initial diagnosis is already suspected (corresponding to an experienced radiologist using the system) or may alternatively present additional functions which further assist the user to find an initial diagnosis (corresponding rather to a unexperienced radiologist).

A medical guideline or clinical guideline is a document with the aim of guiding decisions and criteria regarding diagnosis, management, and treatment in specific areas of healthcare. Modern clinical guidelines identify, summarize and evaluate the highest quality evidence and most current data about prevention, diagnosis, prognosis, therapy including dosage of medications, risk/benefit and cost-effectiveness. They define most important questions related to clinical practice and identify all possible decision options and their outcomes. Guidelines may contain decision or computation algorithms to be followed. Thus, they integrate the identified decision points and respective courses of action with the clinical judgment and experience of practitioners. Some guidelines may place treatment alternatives into classes to help providers in deciding which treatment to use. One major objective of clinical guidelines is to standardize medical care, to raise quality of care, to reduce several kinds of risk (to the patient, to the healthcare provider, to medical insurers and health plans) and to achieve the best balance between cost and medical parameters such as effectiveness, specificity, sensitivity, resolutiveness, etc. Guidelines are usually produced at national or international levels by medical associations or governmental bodies, such as the United States Agency for Healthcare Research and Quality. Local healthcare providers may produce their own set of guidelines or adapt them from existing top-level guidelines.

The retrieved medical information may comprise data indicative of: medical information associated with the patient, e.g. medical images, laboratory test results or prior diagnoses from the patient history file; medical information associated with one or more further patients, e.g. medical images of one or more further patients which comprise anatomical similarities to the patients anatomy; and/or expert medical knowledge, especially expert medical knowledge related to the patient, e.g. scientific and/or medical publications as collected in the international public MEDLINE database which might serve as background information for the diagnosis of the patient or which might assist in deducing correct findings for the patient. Therefore, the system retrieves medical information based on the associated frame of reference, such as the patient or the healthcare professional.

The system, based on the first output and the first node, may identify a further radiologist (or another healthcare professional) and cause the user device to facilitate the radiologist to communicate therewith. Thus, enabling the radiologist (or another healthcare professional) to solicit a second opinion regarding a case.

The system may, additionally or alternatively, process the retrieved medical information to be presented based on a predetermined parameter, and thereafter cause at least a part of the processed medical information to be presented. The predetermined parameter may, for example, comprise: data acquired on the basis of monitoring of prior actions of the radiologist while navigating at least one of the plurality of decision trees to analyse medical information; and/or data indicative of a protocol associated with a medical condition. The protocol may for example be defined in a medical guideline and may correspond to a defined catalogue or list of actions corresponding to image and/or information analysis corresponding to an initial suspicion or clinical request.

The system, in response to navigation of the identified decision tree from the root node to the leaf nodes, may prepare a report or medical report based on the navigation path from the root node to the one of the plurality of leaf nodes. A medical report my comprise medical findings and/or results of interpretation of relevant medical information contained in a medical patient history file, especially medical findings deduced by analysing and interpreting medical image data of the patient. A medical report may comprise an unstructured free-form text report, but also a structured report, e.g. a structured report corresponding to the DICOM standard. Therefore, the system enables, for example, a diagnostic and/or a therapeutic report to be prepared based on the navigation of the identified decision tree, thus reducing burden on healthcare professionals. The prepared report may be circulated internally with professionals associated with the healthcare network, or externally with patients, professionals and/or clinical collaboration partners. The report may, for example, be a decision report comprising data identifying an outcome of a clinical process, such as diagnostic step, and/or a structured report comprising data identifying navigation from the root node to the one of the leaf nodes setting out the rationale for reaching the decision.

In a second embodiment, there is provided a method of controlling operation of a user device, the user device being configured for use by a radiologist when analysing medical information associated with a patient, the method comprising:

maintaining, in a database, an association between a medical condition and at least one of a plurality of decision trees, each decision tree comprising a plurality of nodes organised in a tree structure originating at a root node and terminating at a plurality of leaf nodes via a plurality of branch nodes, wherein the root node and each of the branch nodes have a plurality of outputs, each of the plurality of outputs links a node of the plurality of nodes to a further node of the plurality of nodes and wherein each output causes operation of the user device to be differently controlled;

in response to receiving medical information associated with the patient, identifying, based on the association, a decision tree from the plurality of decision trees; and for the root node of the identified decision tree, performing a process comprising:

in response to receiving data indicative of a first of a plurality of outputs in connection with the root node, selecting a first of the plurality of nodes;

causing the user device to retrieve medical information from at least one of a plurality of data sources based on the first node; and causing at least a part of the retrieved medical information to be displayed on the user device.

In a third embodiment, there is provided a computer program comprising a set of instructions, which, when executed by a computerised device, cause the computerised device to perform a method of controlling operation of a user device, the user device being configured for use by a radiologist when analysing medical information associated with a patient, the method comprising, at the computerised device:

maintaining, in a database, an association between a medical condition and at least one of a plurality of decision trees, each decision tree comprising a plurality of nodes organised in a tree structure originating at a root node and terminating at a plurality of leaf nodes via a plurality of branch nodes, wherein the root node and each of the branch nodes have a plurality of outputs, each of the plurality of outputs links a node of the plurality of nodes to a further node of the plurality of nodes and wherein each output causes operation of the user device to be differently controlled;

in response to receiving medical information associated with the patient, identifying, based on the association, a decision tree from the plurality of decision trees; and for the root node of the identified decision tree, performing a process comprising:

in response to receiving data indicative of a first of a plurality of outputs in connection with the root node, selecting a first of the plurality of nodes;

causing the user device to retrieve medical information from at least one of a plurality of data sources based on the first node; and causing at least a part of the retrieved medical information to be displayed on the user device.

The computer program may, for example, be comprised on a computer operable medium, such as a CD-ROM, a flash memory, a USB memory and/or a USB dongle, and/or may be provisioned electronically over a wired or wireless communications medium.

In a fourth embodiment, there is provided a system operable to control operation of a user device, the user device being configured for use by a radiologist when analysing medical information associated with a patient, the system comprising at least one processor and at least one memory including computer program code, the at least one memory and the computer program code configured to, with the at least one processor, cause the system at least to perform:

maintaining, in a database, an association between a medical condition and at least one of a plurality of decision trees, each decision tree comprising a plurality of nodes organised in a tree structure originating at a root node and terminating at a plurality of leaf nodes via a plurality of branch nodes, wherein the root node and each of the branch nodes have a plurality of outputs, each of the plurality of outputs links a node of the plurality of nodes to a further node of the plurality of nodes and wherein each output causes the system to differently control operation of the user device;

in response to receiving medical information associated with the patient, identifying, based on the association, a decision tree from the plurality of decision trees; and for the root node of the identified decision tree, performing a process comprising:

causing the user device to retrieve medical information from at least one of a plurality of data sources based on a combination of the root node and a state parameter, the state parameter being indicative of one of different stages associated with a determination regarding a first output in connection with the root node;

causing at least a part of the retrieved medical information to be displayed on the user device; and in response to receiving data indicative of the first output, selecting a first of the plurality of nodes.

As described above, the state parameter is indicative of a stage intermediate between a current node and a successive node of the identified decision tree. The state parameter is indicative of an analysis stage intermediate two nodes, and using it the system is able to retrieve and update relevant medical information as the radiologist (or another healthcare professional) navigates between successive nodes via one or more intermediate stages. Therefore, the system advantageously integrates disparate data sources based on the information required by radiologists or another healthcare professional at every stage of analysis.

The system may repeat the above process for each of the nodes successive to the first node of the identified decision tree, and thereby enable the radiologist (or another healthcare professional) to navigate the identified decision tree from the root node to the leaf nodes. Therefore, the system presents relevant medical information relevant for every node and intermediate stages between successive nodes of the identified decision tree.

The system may additionally identify one or more of a plurality of functions usable for processing the retrieved medical information based on a combination of the state parameter and data indicative of the retrieved medical information, and may cause the user device to provision the identified one or more of the plurality of functions to the radiologist (or another healthcare professional), whereby enabling processing of the retrieved medical information. The identified one or more of the plurality of functions may be presented via a user interface in conjunction with the relevant medical information, thereby reducing burden on a healthcare professional.

The system, in response to receiving an input from the radiologist (or another healthcare professional), may cause the user device to present at least a part of the retrieved medical information based on a combination of the input and the state parameter. The input may, for example, comprise an interaction with the user interface, such as selection of a region of interest, and/or further medical information, such as patient history. Therefore, the system adapts the information presented in accordance with the further information provided thereto.

The system may monitor prior actions of the radiologist (or another healthcare professional) when analysing medical information associated with at least some of the different stages and cause at least a part of the retrieved medical information to be displayed on the user device and/or adapt how the medical information is displayed based on the monitoring. Therefore, the system learns over time the style of working and preferences of a healthcare professional, and adapts the information presented accordingly. A prior action according to at least one embodiment of the invention may e.g. comprise a certain function applied to a medical image of a comparable patient or case at the same stage of the inventive decision process, e.g. a certain measurement tool like a distance measurement tool or a certain display tool like a color changing tool or Cinematic Rendering tool.

The system may, additionally or alternatively, process the retrieved medical information based on the monitoring and cause at least a part of the retrieved medical information to be displayed on the user device. Therefore, the system pre-processes retrieved medical information based on observed behaviour of a professional, thereby increasing their efficiency.

The system may retrieve medical information based on: data indicative of the patient; data indicative of the radiologist (or another healthcare professional); data indicative of a medical condition; data indicative of one or more guidelines; data indicative of one or more legal regulations; data acquired on the basis of monitoring of prior actions of the radiologist while navigating at least one of the plurality of decision trees to analyse medical information; data indicative of a customisation parameter; and/or data indicative of a user setting.

The retrieved medical information may comprise data indicative of: medical information associated with the patient; medical information associated with one or more further patients; and/or expert medical knowledge. Therefore, the system retrieves medical information based on the associated frame of reference, such as the patient or the healthcare professional.

The system, based on the state parameter and the first node, may identify a further radiologist (or another healthcare professional) and cause the user device to facilitate the radiologist to communicate therewith. Thus, enabling the radiologist (or another healthcare professional) to solicit a second opinion regarding a case.

The system, in response to navigation of the identified decision tree from the root node to the leaf nodes, prepare a report based on the navigation path from the root node to the one of the plurality of leaf nodes. Therefore, the system enables a diagnostic and/or therapeutic report to be prepared based on the navigation of the identified decision tree, thus reducing burden on healthcare professionals. The prepared report may be circulated internally with professionals associated with the healthcare network, or externally with patients, professionals and and/or clinical collaboration partners.

In a fifth embodiment, there is provided a method of controlling operation of a user device, the user device being configured for use by a radiologist when analysing medical information associated with a patient, the method comprising:

maintaining, in a database, an association between a medical condition and at least one of a plurality of decision trees, each decision tree comprising a plurality of nodes organised in a tree structure originating at a root node and terminating at a plurality of leaf nodes via a plurality of branch nodes, wherein the root node and each of the branch nodes have a plurality of outputs, each of the plurality of outputs links a node of the plurality of nodes to a further node of the plurality of nodes and wherein each output causes operation of the user device to be differently controlled;

in response to receiving medical information associated with the patient, identifying, based on the association, a decision tree from the plurality of decision trees; and for the root node of the identified decision tree, performing a process comprising:

causing the user device to retrieve medical information from at least one of a plurality of data sources based on a combination of the root node and a state parameter, the state parameter being indicative of one of different stages associated with a determination regarding a first output in connection with the root node;

causing at least a part of the retrieved medical information to be displayed on the user device; and in response to receiving data indicative of the first output, selecting a first of the plurality of nodes.

In a sixth embodiment, there is provided a computer program comprising a set of instructions, which, when executed by a computerised device, cause the computerised device to perform a method of controlling operation of a user device, the user device being configured for use by a radiologist when analysing medical information associated with a patient, the method comprising, at the computerised device:

maintaining, in a database, an association between a medical condition and at least one of a plurality of decision trees, each decision tree comprising a plurality of nodes organised in a tree structure originating at a root node and terminating at a plurality of leaf nodes via a plurality of branch nodes, wherein the root node and each of the branch nodes have a plurality of outputs, each of the plurality of outputs links a node of the plurality of nodes to a further node of the plurality of nodes and wherein each output causes operation of the user device to be differently controlled;

in response to receiving medical information associated with the patient, identifying, based on the association, a decision tree from the plurality of decision trees; and for the root node of the identified decision tree, performing a process comprising:

causing the user device to retrieve medical information from at least one of a plurality of data sources based on a combination of the root node and a state parameter, the state parameter being indicative of one of different stages associated with a determination regarding a first output in connection with the root node;

causing at least a part of the retrieved medical information to be displayed on the user device; and in response to receiving data indicative of the first output, selecting a first of the plurality of nodes.

The computer program may, for example, be comprised on a computer operable medium, such as a CD-ROM, a flash memory, a USB memory and/or a USB dongle, and/or may be provisioned electronically over a wired or wireless communications medium.

In a seventh embodiment, there is provided a system operable to control operation of a user device, the user device being configured for use by a radiologist when analysing medical information associated with a patient, the system comprising at least one processor and at least one memory including computer program code, the at least one memory and the computer program code configured to, with the at least one processor, cause the system at least to perform:

maintaining, in a database, an association between a medical condition and at least one of a plurality of decision trees, each decision tree comprising a plurality of nodes organised in a tree structure originating at a root node and terminating at a plurality of leaf nodes via a plurality of branch nodes, wherein the root node and each of the branch nodes have a plurality of outputs, each of the plurality of outputs links a node of the plurality of nodes to a further node of the plurality of nodes and wherein each output causes the system to differently control operation of the user device;

identifying a plurality of prior actions performed by the radiologist while navigating at least one of the plurality of decision trees to analyse medical information;

in response to receiving medical information associated with the patient, identifying, based on the association, a decision tree from the plurality of decision trees; and for the root node of the identified decision tree, performing a process comprising:

causing the user device to retrieve medical information from at least one of a plurality of data sources based on the root node and to process the retrieved medical information based on the identified prior actions; and causing at least a part of the processed medical information to be displayed on the user device.

Therefore, the system advantageously integrates disparate data sources based on the information required by radiologists at every stage of analysis, and processes the retrieved medical information based on a style of working of the radiologist (or another healthcare professional) or with other words automatically integrates user preferences operating the system in every stage of analysis, thereby increasing efficiency.

The system, in response to receiving data indicative of a first of a plurality of outputs in connection with the root node, may select a first of the plurality of nodes, thereby enabling navigation from the root node to a successive node. The system may repeat the above process for each of the nodes successive to the root node of the identified decision tree, and thereby enable the radiologist (or another healthcare professional) to navigate the identified decision tree from the root node to the leaf nodes. Therefore, the system processes the retrieved medical information at every stage of analysis, thereby customising presented information in accordance with the style of working of the radiologist (or another healthcare professional).

The system may maintain a state parameter indicative of a stage associated with a determination of a second output in connection with the root node, i.e. a current stage of analysis. The system may cause the user device to present at least part of the retrieved medical information based on the state parameter. The state parameter may, for example, be indicative of a stage intermediate between a current node and a successive node of the identified decision tree.

The system may additionally identify one or more of a plurality of functions usable for processing the retrieved medical information based on a combination of the root node and the identified prior actions. The system may use at least one of the functions for processing the retrieved medical information. For example, if a radiologist prefers to analyse scans in a specific resolution, using a certain color mapping and/or prefers a specific view angle on medical image data, then the system may process the retrieved medical information so as to change the resolution, the color mapping and/or the view angle of scans and/or the image data automatically, accordingly.

The system may, additionally or alternatively, cause the user device to provision the identified one or more of the plurality of functions to the radiologist (or another healthcare professional), whereby enabling processing of the retrieved medical information. The identified one or more of the plurality of functions may be presented via a user interface in conjunction with the relevant medical information, thereby reducing burden on a healthcare professional.

The system, in response to receiving an input from the radiologist (or another healthcare professional), may cause the user device to present at least a part of the retrieved medical information based on a combination of the input and the identified prior actions. The input may, for example, comprise an interaction with the user interface, such as selection of a region of interest, and/or further medical information, such as patient history. Therefore, the system adapts the information presented in accordance with the further information provided thereto.

The system may cause the user device to process the retrieved medical information based on: data associated with the patient; data associated with another patient; data indicative of the radiologist; data indicative of a medical condition; data indicative of one or more guidelines; data indicative of one or more legal regulations; data indicative of a customisation parameter; and/or data indicative of a user setting. Therefore, the system uses the associated frame of reference for pre-processing the retrieved medical information.

The system may retrieve medical information based on: data indicative of the patient; data indicative of the radiologist (or another healthcare professional); data indicative of a medical condition; data indicative of one or more guidelines; data indicative of one or more legal regulations; data acquired on the basis of monitoring of prior actions of the radiologist while navigating at least one of the plurality of decision trees to analyse medical information; data indicative of a customisation parameter; and/or data indicative of a user setting.

The retrieved medical information may comprise data indicative of: medical information associated with the patient; medical information associated with one or more further patients; and/or expert medical knowledge. Therefore, the system retrieves medical information based on the associated frame of reference, such as the patient or the healthcare professional.

The system, based on the identified prior actions, may identify a further radiologist (or another healthcare professional) and cause the user device to facilitate the radiologist to communicate therewith. Thus, enabling the radiologist (or another healthcare professional) to solicit a second opinion regarding a case.

In an eighth embodiment, there is provided a method of controlling operation of a user device, the user device being configured for use by a radiologist when analysing medical information associated with a patient, the method comprising:

maintaining, in a database, an association between a medical condition and at least one of a plurality of decision trees, each decision tree comprising a plurality of nodes organised in a tree structure originating at a root node and terminating at a plurality of leaf nodes via a plurality of branch nodes, wherein the root node and each of the branch nodes have a plurality of outputs, each of the plurality of outputs links a node of the plurality of nodes to a further node of the plurality of nodes and wherein each output causes operation of the user device to be differently controlled;

identifying a plurality of prior actions performed by the radiologist while navigating at least one of the plurality of decision trees to analyse medical information;

in response to receiving medical information associated with the patient, identifying, based on the association, a decision tree from the plurality of decision trees; and for the root node of the identified decision tree, performing a process comprising:

causing the user device to retrieve medical information from at least one of a plurality of data sources based on the root node and to process the retrieved medical information based on the identified prior actions; and causing at least a part of the processed medical information to be displayed on the user device.

In a ninth embodiment, there is provided a computer program comprising a set of instructions, which, when executed by a computerised device, cause the computerised device to perform a method of controlling operation of a user device, the user device being configured for use by a radiologist when analysing medical information associated with a patient, the method comprising, at the computerised device:

maintaining, in a database, an association between a medical condition and at least one of a plurality of decision trees, each decision tree comprising a plurality of nodes organised in a tree structure originating at a root node and terminating at a plurality of leaf nodes via a plurality of branch nodes, wherein the root node and each of the branch nodes have a plurality of outputs, each of the plurality of outputs links a node of the plurality of nodes to a further node of the plurality of nodes and wherein each output causes operation of the user device to be differently controlled;

identifying a plurality of prior actions performed by the radiologist while navigating at least one of the plurality of decision trees to analyse medical information;

in response to receiving medical information associated with the patient, identifying, based on the association, a decision tree from the plurality of decision trees; and for the root node of the identified decision tree, performing a process comprising:

causing the user device to retrieve medical information from at least one of a plurality of data sources based on the root node and to process the retrieved medical information based on the identified prior actions; and causing at least a part of the processed medical information to be displayed on the user device.

The computer program may, for example, be comprised on a computer operable medium, such as a CD-ROM, a flash memory, a USB memory and/or a USB dongle, and/or may be provisioned electronically over a wired or wireless communications medium.

Unless defined otherwise, all technical terms used herein have the same meaning as commonly understood by one of ordinary skill in the art to which the examples pertain. Above term definitions given with regard to a certain embodiment of the present invention do likewise apply for any other embodiment, if not explicitly excluded.

Referring to FIG. 1, there is shown schematically an example of a healthcare network 100. The healthcare network 100 comprises a number of systems. The term "system" is used herein to denote an entity (or entities) in the healthcare network 100. A system may be embodied in the form of apparatus, hardware, software, a function, a virtualized resource, etc., or any combination of same. A healthcare network can comprise at least some different and/or additional components to those shown in FIG. 1.

The healthcare network 100 comprises one or more user devices 101a-n configured for use by a radiologist when analysing medical information associated with a patient. The user devices 101a-n may comprise a smart watch, a smart telephone, a tablet computer, a personal computer and/or be embodied as an advanced visualization (AV) station comprising more than one display screen as typically present in a radiology department of a hospital or medical centre. The user devices 101a-n may comprise an application for presenting medical information to a radiologist. The medical information may be provided and/or displayed via a user interface as described in more detail with reference to FIGS. 7 to 16. Preferably, the medical information may be displayed via the display screen of the user device 101a-n. At least some of the user devices 101a-n may be communicatively coupled to each other via, for example, a local area network, metropolitan area network or a wide area network, and may have access to systems external to the healthcare network 100 via a Candidate Access Network (CAN) (not shown). The user devices 101a-n may comprise one or more processors (not shown) for performing various data processing operations according to embodiments and/or one or more memories (not shown) for storing various data according to embodiments.

The CAN may, for example, be a wireless access network or a wired access network. Examples of wireless access networks include, but are not limited to, Wireless Local Area Networks (WLANs) and mobile radio access networks. An example of a mobile radio access network is an Evolved Universal Terrestrial Radio Access Network (E-UTRAN). An example of a wired access network is an Asymmetric Digital Subscriber Line (ADSL).

The healthcare network 100 may additionally comprise one or more servers (not shown) configured to provision applications and data to the user devices 101a-n, a plurality of data sources 107a-n configured to provision medical information, a specialist user terminal (for example, a nurse call system an advanced visualization station or the like) and/or one or more medical devices (for example, an ultra-sound system, Computed Tomography system, a Nuclear Magnetic Resonance system or the like).

The data sources 107a-n may comprise a mix of disparate proprietary and off-the-shelf data sources. The data sources 107a-n may, for example, include a picture archiving and communication system (PACS), an electronic medical records (EMR), an emergency care summary (ECS), a key information summary (KIS), an electronic patient record (EPR), a personal health record (PHR), a hospital and/or radiology information system (HIS/RIS) and/or an expert system, like the public MEDLINE database.

At least some of the user devices 101a-n have access to a system 103 for controlling operation thereof. The system 103 may be implemented on a single computer or a network of computers. In examples, the system 103 may be a central or location-specific distributed system. The system 103 comprises one or more processors (not shown) for perform-ing various data processing operations according to embodi-ments. The system 103 comprises or otherwise has access to a database 105 for storing various data according to embodi-ments. The database 105 may comprise one or more memo-ries (not shown). The memory may be volatile so that data stored therein may need to be re-learnt upon failure/re-boot.

The database 105 maintains an association between a medical condition and at least one of a plurality of decision trees. Each of the decision trees comprise a plurality of nodes organised in a tree structure originating at a root node and terminating at a plurality of leaf nodes via a plurality of branch nodes, in which the root node and each of the branch nodes have a plurality of outputs that link a node to a further node. Each of the outputs causes the system 103 to differ-ently control operation of the user devices 101a-n. The decision trees define at least two clinical process paths leading to a diagnosis of a medical condition for a patient, wherein each of the nodes is a diagnostic stage in the clinical process, wherein each stage in the clinical process may be based on or defined by a medical guideline relevant for the patient, a clinical request procedure as defined by or as based on an initial suspicion, an initial medical question or indi-cation and/or an initial suspicion which lead to the further examination of the patient, e.g. to an image acquisition procedure. Thus, also the used imaging modality or the imaging protocol may be used to define and/or chose a process path and/or nodes of the decision tree.

Figure 2:
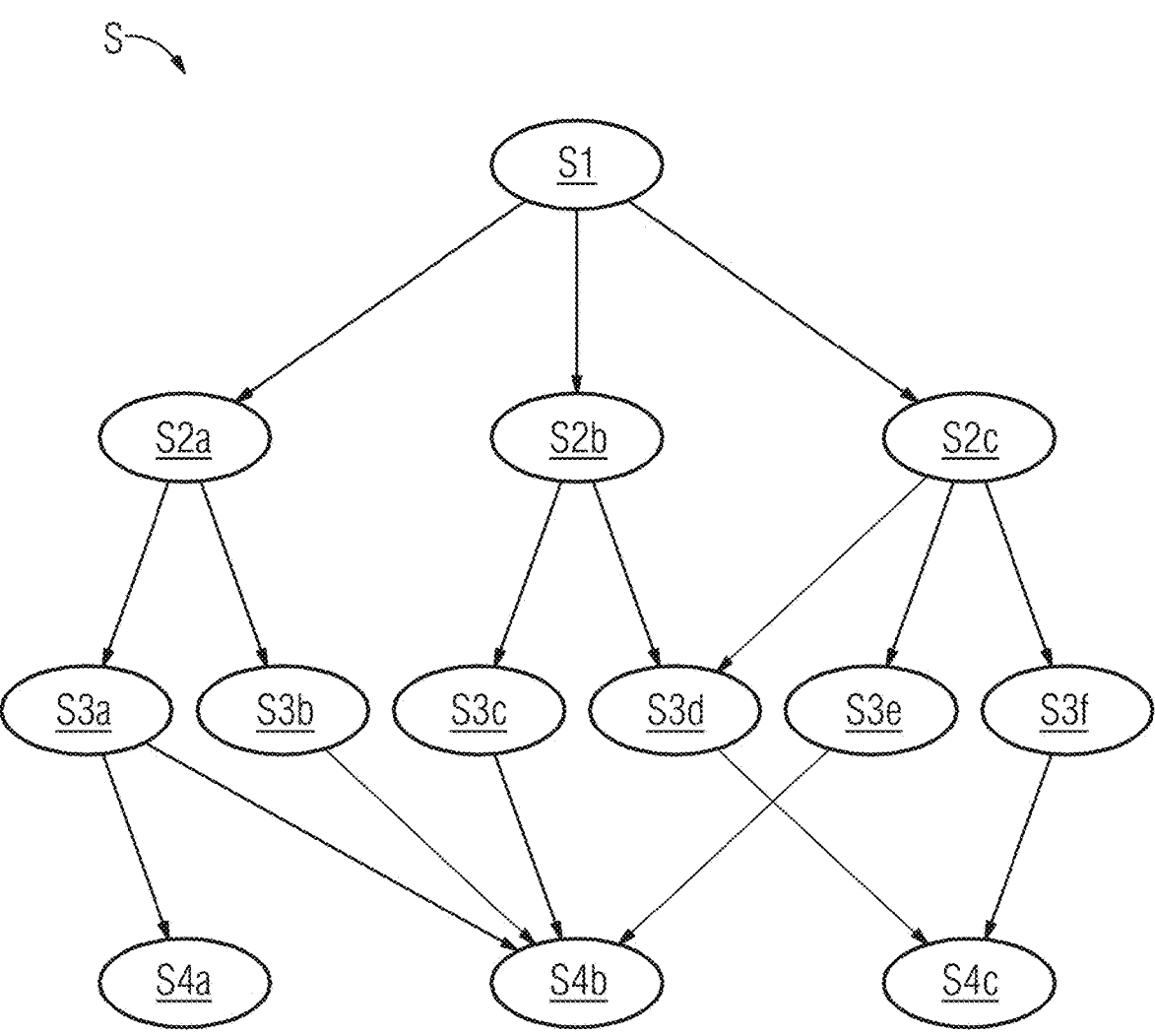
FIG. 2 shows an example decision tree in accordance with embodiments.

Referring to FIG. 2, there is shown an example decision tree S comprising a root node S1, a plurality of branch nodes S2a-c and S3a-f, and a plurality of leaf nodes S4a-c. The leaf nodes S4a-c may be indicative of one or more medical conditions, thereby associating the decision tree S with the medical conditions identified by the leaf nodes S4a-c. Each path from the root node S1 to the leaf nodes S4a-c may indicate diagnostic stages involved in a clinical process involved in determining a medical condition.

The root node S1 and the branch nodes S2a-c and S3a-f each have a plurality of outputs that link it with a different one of the branch or leaf nodes S2a-c, S3a-f or S4a-c. For example, various outputs link the root node S1 with the branch nodes S2a-c. The outputs may be based on an input from a radiologist analysing medical information associated with a patient.

Figure 3:
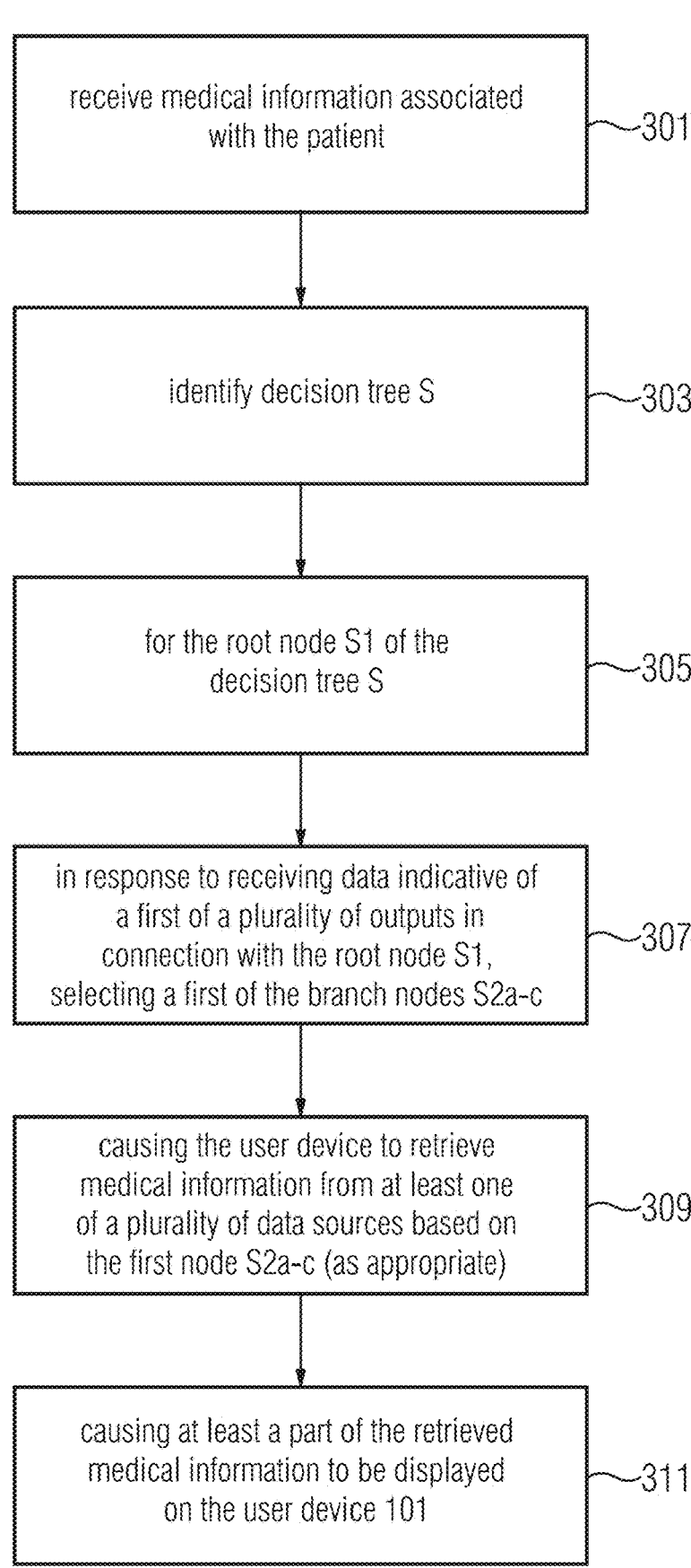
FIG. 3 shows a flow diagram depicting an example of processing data in accordance with embodiments.

In the example set forth in FIG. 3, the system 103 controls operation of the user device 101 when operated by a radiologist analysing medical information associated with a patient. In this example, the system 103 receives medical information associated with the patient (block 301). The medical information associated with the patient may, for example, be received by the system 103 in response to an event, including: the radiologist selecting the case for analy-sis; availability of a diagnostic report; and/or upcoming appointment of the radiologist with the patient. The medical information associated with the patient may, for example, include medical images, image data sets and/or medical image studies from image acquisition scans acquired using at least one of above introduced medical imaging modalities and healthcare information associated with the patient, e.g. provided from PACS, HIS and/or RIS of the medical facility the radiologist is working at.

In response to receiving medical information associated with the patient, the system 103 identifies a decision tree based on the aforementioned association between the deci-sion trees and medical conditions. In this example, the system 103 identifies the decision tree S (block 303).

For the root node S1 (block 305), the system 103 causes the user device 101, or an application executing at least partially thereon (alternatively executing on central or local server, or in cloud), to present medical information associ-ated with the patient for consideration by the radiologist (or another healthcare professional). The application may be understood as a software program providing for the display of medical information, the provision of manipulation, input and/or analysing measures or tools. The presented medical information may comprise all or part of the received medical information, and/or medical information different to the received medical information. The radiologist may analyse the presented medical information and decide on a first of a plurality of outputs which link the root node S1 with one of the branch nodes S2a-c. The radiologist's analysis may preferably comprise manipulation/evaluation/analysis of recent medical images related to the patient, e.g. identifica-tion and/or measurement of lesions, organs, anatomical structures and/or tissues, but also prior imaging studies of the patient and/or laboratory test results contained in the patient history file. Preferably, the radiologist may enter the analysis-based decision on the first one of a plurality of outputs via the user interface to the system 103 or to the user device 101, e.g. by entering result information via mouse, keypad, microphone or the like.

In response to receiving from the user data indicative the first output in connection with the root node S1, the system 103 selects a first of the branch nodes S2a-c (block 307), whereby advancing diagnosis to a next stage. For example, the received medical information may indicate a potentially cancerous lesion in a patient's body, and as a first step the radiologist may assess scan images to identify organ(s) affected by the lesion.

The system 103 causes the user device 101 to retrieve medical information from one or more of the data sources 107a-n (block 309). The retrieved medical information is based on the first node S2a-c (as appropriate). For example, if the radiologist determines that the lesion affects the prostate gland, the system 103 may cause the user device 101 to retrieve medical information relevant for the assessment of potentially cancerous lesions affecting the prostate gland, e.g. image data of another patient related to a similar medical indication. Therefore, embodiments flexibly integrate disparate data sources in the healthcare network 100. The integration is based on outputs linking nodes in the decision trees and medical information relevant for further assessment in the clinical process.

The system 103 causes at least a part of the retrieved medical information to be displayed on the user device 101 (block 311). Therefore, enabling the radiologist to continue analysis of medical information associated with the patient.

In some arrangements, the system 103 repeats blocks 307-311 for each of the nodes successive to the aforementioned first node S2a-c (as appropriate), thereby enabling the radiologist to navigate the identified decision tree S from the root node S1 to the leaf nodes S4a-c. Therefore, embodiments assist the radiologist at every stage of diagnosis by retrieving and presenting relevant medical information.

In embodiments, the system 103, based on a combination of the first output at block 307 and data indicative of the medical information retrieved at block 309, causes the user device 101 to identify one or more of a plurality of functions usable for processing the retrieved medical information. The functions may, for example, include a function for assessing change in dimensions of lesions over time and a function for assessing change in colour profile of lesions over time.

The system 103 causes the user device 101 to provision the identified functions to the radiologist, whereby enabling processing of the medical information retrieved at block 309. Therefore, embodiments provide relevant medical information to the radiologist and provision relevant functions to enable the radiologist to process the medical information, thereby reducing the cognitive burden on the healthcare professional, and the time it takes with state of the art tools to assess medical conditions. The provisioning of the identified functions may comprise the displaying of an activation/operation button for the identified function via the user interface, so that the user enabled to start, operate, use or apply the identified function to displayed medical information. The provisioning of the identified function may comprise the addition of a tool button corresponding to the identified function in a list of tools provided by the application, which may then be selected by the user via the user interface. Alternatively, the identified function may automatically be applied to the medical information displayed upon identification. This may also depend on user preferences or the configuration of the inventive system.

Figure 4:
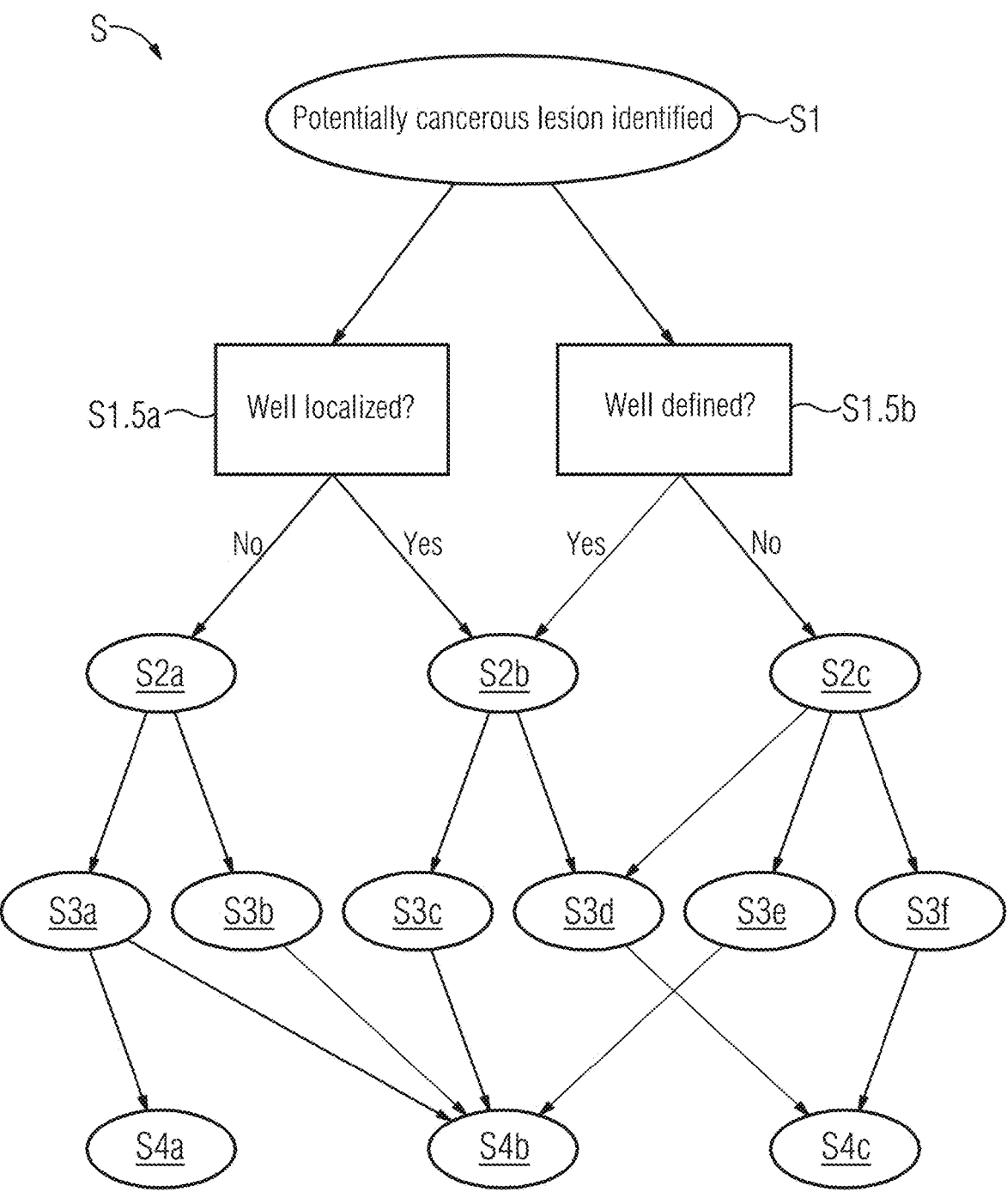
FIG. 4 shows an example decision tree in accordance with embodiments.
Figure 7:
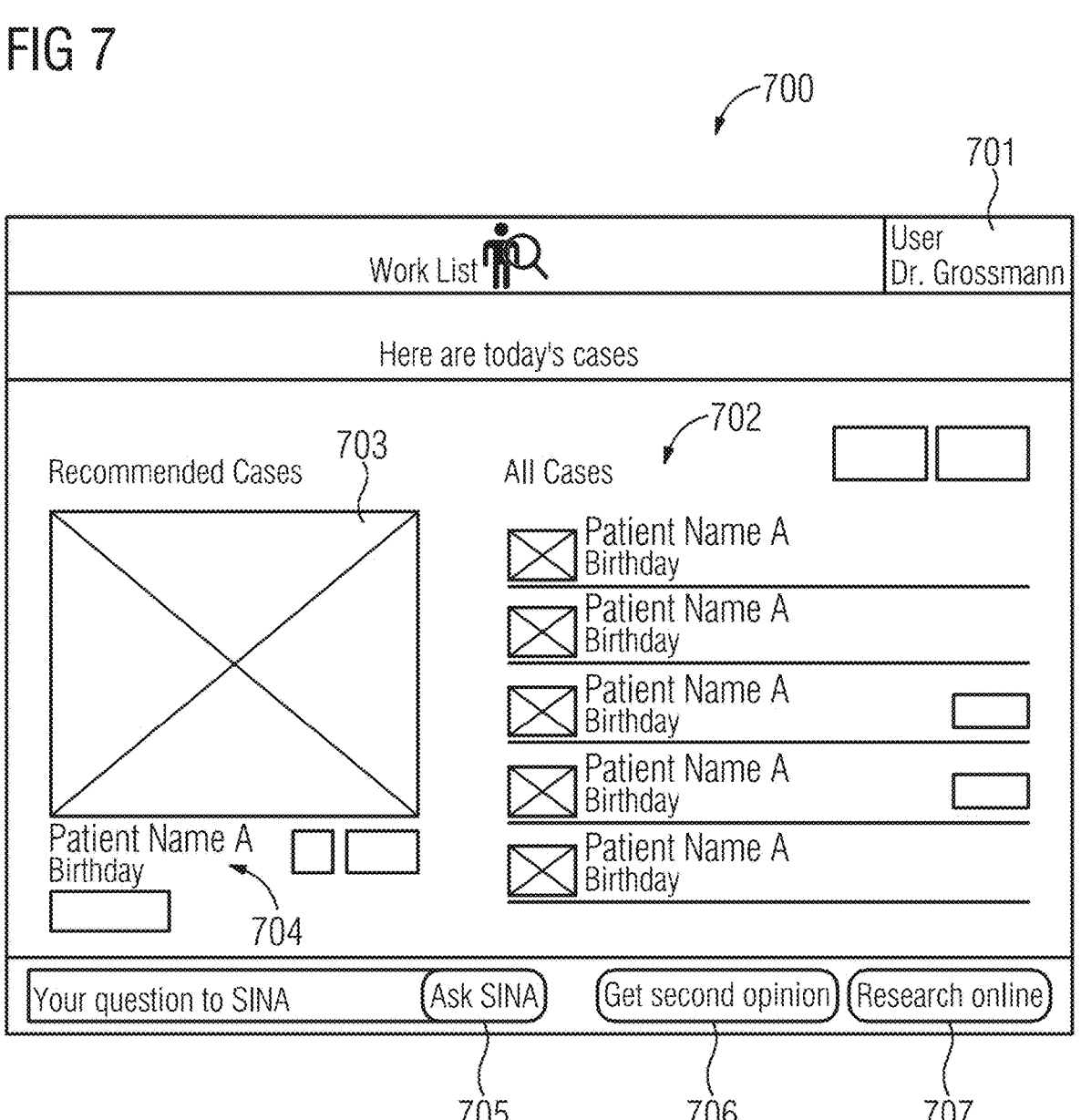

In embodiments, the system 103 may maintain a state parameter indicative of a stage intermediate between a current node and a successive node of the identified decision tree. In the example set forth in FIG. 4, intermediate the root node S1 and the branch nodes S2a-c there are two intermediate stages for controlling transition therebetween. In this example, the radiologist identifies a potentially cancerous lesion as part of assessment in connection with the root node S1. Subsequently, the radiologist assesses whether the identified lesion is well localised, i.e. the identified lesion is limited to an organ (such as the prostate gland), and does not extend beyond that one organ (intermediate stage S1.5a). The radiologist additionally considers whether the identified lesion is well defined, i.e. the edges of the identified lesion are reasonably sharp and clearly define its extent (intermediate stage S1.5b). Based on the outcome of the assessment the intermediate stages S1.5a and S1.5b, the system 103 selects one of the branch nodes S2a-c.

In this example, the state parameter may indicate the intermediate stage S1.5a or S1.5b associated with a determination of the first output in connection with the root node S1. Similarly, there may be stages intermediate the first node S2a-c (as appropriate) and a successive node, and in which case the state parameter may be indicative of a stage associated with a determination of a second output in connection with the first node S2a-c (as appropriate).

The system 103 may cause the user device 101 to present at least a part of the medical information retrieved at block 309 based on the state parameter. Therefore, embodiments present medical information relevant for a current stage of analysis, and thereby reduce the cognitive burden.

The system 103 may, in response to receiving an input from the radiologist, cause the user device 101 to present at least a part of the medical information retrieved at block 309 based on a combination of the input and state parameter. For example, the radiologist at the intermediate stage S1.5a may assess medical images, i.e. medical scans in relation to regions neighbouring the prostate gland by interacting with the currently presented medical information, and the system 103 causes the user device 101 to update the previously presented medical information based on the interactions and the state parameter, thereby maintaining relevance of the presented medical information for a current stage of assessment and for what the radiologist is doing.

In some arrangements, the medical information is retrieved at block 309 based on: data indicative of the patient; data indicative of the radiologist; data indicative of a medical condition; data indicative of one or more guidelines; data indicative of one or more legal regulations; data acquired on the basis of monitoring of prior actions of the radiologist while navigating at least one of the plurality of decision trees to analyse medical information; data indicative of a customisation parameter; and/or data indicative of a user setting. Therefore, embodiments retrieve relevant medical information based on associated context and/or user preference. The customization parameter may be in the form of a default setting, which may be actively chosen or changed by a user or which may automatically change over time depending on user input/interaction with the system.

In embodiments, the medical information retrieved at block 309 comprises data indicative of: medical information associated with the patient; medical information associated with one or more further patients; and/or expert medical knowledge. The system 103 may, for example, cause further relevant medical information related to the patient to aid analysis and/or for analysis in relation to a comorbidity. The system 103 may, additionally or alternatively, retrieve medical information corresponding to other patients with similar symptoms and/or conditions. The system 103 may, additionally or alternatively, retrieve expert medical information from, for example, scientific journals from medical expert databases to aid the radiologist with his assessment. Therefore, embodiments provide comprehensive medical information relevant for a current stage of analysis.

In some arrangements, the system 103, based at least on the aforementioned first output in connection with the root node S1 and the aforementioned first node S2a-c (as appropriate) selected at block 307, identifies a further radiologist or another healthcare professional. For example, the further radiologist or healthcare professional may be an expert or a colleague with bandwidth to have formal or informal discussions regarding the case under consideration. The system 103 may cause the user device 101 to facilitate communication between the radiologist and the further radiologist. Therefore, embodiments enable collaboration between radiologists in order to improve diagnosis.

In embodiments, the system 103 processes at least a part of the medical information retrieved at block 309 based on a predetermined parameter, and thereafter causes at least a part of the processed medical information to be displayed on the user device 101. The predetermined parameter may, for example, comprise or be based on: data acquired on the basis of monitoring of prior actions of the radiologist while navigating at least one of the plurality of decision trees to analyse medical information; and/or data indicative of a protocol associated with a medical condition. Therefore, embodiments customise retrieved medical information in accordance with the radiologist's preferences or style of working, and/or based on relevant guidelines or protocols.

In some arrangements, in response to navigation of the identified decision tree from the root node S1 to the leaf nodes S4a-c, the system 103 prepares a report based on a navigation path from the root node S1 to one of the leaf nodes S4a-c (as appropriate). The report may, for example, be a decision report comprising data indicative of a clinical stage, such as a diagnostic test. The report may, alternatively, be a structured report comprising data indicative of the clinical path setting out various stages of assessment of the received medical information and conclusion of the radiologist as regards the medical condition. Structured reports, like a DICOM structured report, follow a pre-defined template, and comprise analysis regarding decisions at every stage of analysis. The report may be for internal circulation within the healthcare network, and/or may be circulated externally with patients, healthcare service providers, healthcare professionals and/or clinical collaboration partners. In examples, the reports may be anonymised before external circulation, and may, for example, serve as an input to: a statistical decision support system, a clinical decision support system, an expert system, and/or a healthcare population management system.

In some embodiments, the aforementioned outputs in connection with the root node S1 and the branch nodes S2a-c and S3a-f correspond to an output from a medical domain, i.e. the outputs are indicative of an outcome of a medical consideration In the example set forth in FIG. 5, the system 103 controls operation of the user device 101 when operated by a radiologist analysing medical information associated with a patient. Responsive to receiving medical information (block 301), the system 103 identifies a decision tree based on the aforementioned association between the decision trees and medical conditions. In this example, the system 103 identifies the decision tree S (block 303). Blocks 301 and 303 are identical to identically numbered blocks in FIG. 3.

For the root node S1 (block 501), the system 103 may cause the user device 101, or an application executing thereon, to retrieve medical information from one or more of the data sources 107a-n based on a combination of the root node S1 and the aforementioned state parameter (block 503). As described above, the state parameter is indicative of a stage intermediate between a current node, i.e. the root node S1 in this example, and a successive node, i.e. one of the branch nodes S2a-c in this example, of the identified decision tree. With reference to example set forth in FIG. 4, the state parameter may, for example, be indicative of the intermediate stages S1.5a or S1.5b shown in FIG. 4.

The system 103 may cause at least a part of the retrieved medical information to be displayed on the user device 101 (block 505). The system 103 therefore retrieves medical information relevant for analysis in relation to a current stage of analysis, and as a consequence presents relevant medical information in real time. The system 103, responsive to receiving data indicative of the first output in connection with the root node S1, selects a first of the plurality of linked branch nodes S2a-c.

Therefore, embodiments in accordance with FIG. 5 flexibly integrate input from disparate data sources 107a-n in a healthcare network based on medical information that is relevant for assessment in respect of a current stage in the clinical process.

The system 103 may repeat blocks 503-507 for each of the nodes successive to the aforementioned first node S2a-c (as appropriate), thereby enabling the radiologist to navigate the identified decision tree S from the root node S1 to the leaf nodes S4a-c. Therefore, embodiments assist the radiologist at every stage of diagnosis by retrieving and presenting relevant medical information.

In embodiments, the system 103, based on a combination of the state parameter and data indicative of the medical information retrieved at block 503, may cause the user device 101 to identify one or more of a plurality of functions usable for processing the retrieved medical information. The functions may, for example, include a function for calculating dimensions of lesions identified in a medical scan, functions for measuring distances to reference points or landmarks, rendering functions to advantageously display certain tissues and/or anatomical structures, functions for color mapping, functions for displaying image data under a preferred view angle or the like.

The system 103 may cause the user device 101 to provision the identified functions to the radiologist, whereby enabling processing of the medical information retrieved at block 503. Therefore, embodiments provision relevant tools concurrent with provisioning of relevant medical information, e.g. the tools serve medical image manipulation, display and/or image analysis steps via the user interface.

The system 103, in response to receiving an input from the radiologist, may cause the user device 101 to present at least a part of the medical information retrieved at block 503 based on a combination of the input and the state parameter. Therefore, embodiments update relevant medical information based on the radiologist's interaction in connection with the medical information that is currently presented.

In some arrangements, the system 103 can monitor prior actions of the radiologist when analysing medical information associated with at least some of the different stages associated with a determination regarding a first output in connection with the root node S1. The system 103, based on the monitoring of the prior actions, causes at least a part of the medical information retrieved at block 503 to be displayed on the user device in a tailored manner. Therefore, embodiments customise the information presented in accordance with radiologists' style and/or preferences of working, and as a consequence are capable of personalising the display of medical information, e.g. certain functions are initially displayed for activation by the radiologist at a node within the decision tree, as he/she is usually using this function at this stage of the decision process.

The system 103 may, additionally or alternatively process the medical information retrieved at block 503 based on the monitoring of the prior actions. For example, if the system determines that the radiologist changes the scanned images to a certain resolution, then the system 103 may process subsequently received scanned images to that same resolution. The system 103 may then cause at least part of subsequently processed medical information to be displayed on the user device 101.

In some embodiments, the medial information is retrieved at block 503 based on: data indicative of the patient; data indicative of the radiologist; data indicative of a medical condition; data indicative of one or more guidelines; data indicative of one or more legal regulations; data acquired on the basis of monitoring of prior actions of the radiologist while navigating at least one of the plurality of decision trees to analyse medical information; data indicative of a customisation parameter; and/or data indicative of a user setting. Therefore, embodiments retrieve relevant medical information based on associated context and/or user preference.

In some arrangements, the medial information retrieved at block 503 comprises data indicative of: medical information associated with the patient; medical information associated with one or more further patients; and/or expert medical knowledge.

Similar to the example set forth in FIG. 3, the system 103 may identify a further radiologist or another healthcare professional based on the state parameter and the current node, i.e. one of the branch nodes S2*a*-*c*, for collaboration. The system may, additionally or alternatively, prepare a report responsive to navigation of the identified decision tree S from the root node S1 to the leaf nodes S4*a*-*c*.

In response to navigation of the identified decision tree from the root node (S1) to the leaf nodes (S4*a*-*c*), the system 103 may prepare a report based on a navigation path from the root node (S1) to the one of the plurality of leaf nodes (S4*a*-*c*).

In the example set forth in FIG. 6, the system 103 controls operation of the user device 101 when operated by a radiologist analysing medical information associated with a patient.

The system 103 identifies a plurality of prior actions performed by the radiologist while navigating at least one of the decision trees to analyse medical information (block 601). The system 103 may monitor actions performed by a radiologist for identify habits, preferences and style of working of the radiologist. The system 103 may identify the prior actions at block 601 based on this monitoring. The prior actions may be associated with nodes, decision trees and/or stages associated with various clinical processes, and the identification of the prior actions may be based on this association. An example prior action may for example be: Nuclear Magnetic Resonance image data sets are always displayed and/or analysed using a certain resolution, zooming factor and/or color mapping.

The system 103, responsive to receiving medical information associated with a patient (block 301), identifies a decision tree based on the aforementioned association between the decision trees and medical conditions. In this example, the system 103 identifies the decision tree S (block 303). Blocks 301 and 303 are identical to identically numbered blocks in FIG. 3.

For the root node S1 (block 603), the system 103 may cause the user device 101, or an application executing thereon, to retrieve medical information from one or more of the data sources 107*a*-*n* based on a combination of the root node S1 and the prior actions identified at block 601 (block 605). Embodiments in accordance with FIG. 6 therefore process the retrieved medical information so as to customise it based on the radiologist's style of working.

The system 103 causes at least a part of the medical information processed at block 605 to be displayed on the user device 101 (block 607). Therefore, embodiments improve the user experience by automatically personalising information displayed in accordance with individual habits, preferences and style of working.

In response to data indicative of a first of a plurality of outputs in connection with the root node S1, the system 103 selects a first of the plurality of linked nodes S2*a*-*c*. Thus, enabling the radiologist to navigate the decision tree identified at block 303. The system 103 may, additionally, repeat blocks 605 and 607 for each of the nodes successive to the aforementioned first node S2*a*-*c* (as appropriate), thereby enabling the radiologist to navigate the identified decision tree S from the root node S1 to the leaf nodes S4*a*-*c*. Therefore, embodiments assist the radiologist at every stage of diagnosis by retrieving and presenting relevant medical information.

In some arrangements, the system 103 may cause the user device 101 to present at least a part of the retrieved medical information at block 309 based on the aforementioned state parameter. Therefore, embodiments present medical information relevant for a current stage of analysis, and thereby improving user experience and reducing cognitive burden on the radiologist or another healthcare professional.

In embodiments, the system 103, based on a combination of the root node S1 and data indicative of the prior actions identified at block 601, causes the user device 101 to identify one or more of a plurality of functions usable for processing the retrieved medical information. The system 103 may cause the user device 101 to provision the identified functions to the radiologist, whereby enabling processing of the medical information retrieved at block 605. The system 103 may, additionally or alternatively, use one or more of the identified functions to process the retrieved medical information, and may thereafter cause the user device 101 to present at least a part of the processed medical information.

In embodiments, in response to receiving an input from the radiologist or another healthcare professional, the system 103 causes the user device 101 to present at least a part of the retrieved medical information at block 605 based on a combination of the input and the identified prior actions.

In some arrangements, the system 103 causes the user device 101 to process the medical information retrieved at block 605 based on: data indicative of the patient; data indicative of the radiologist; data indicative of a medical condition; data indicative of one or more guidelines; data indicative of one or more legal regulations; data indicative of a customisation parameter; and/or data indicative of a user setting. Therefore, embodiments pre-process the retrieved medical information in order to aid the radiologist.

In some embodiments, the medial information is retrieved at block 605 based on: data indicative of the patient; data indicative of the radiologist; data indicative of a medical condition; data indicative of one or more guidelines; data indicative of one or more legal regulations; data indicative of a customisation parameter; and/or data indicative of a user setting. Therefore, embodiments retrieve relevant medical information based on associated context and/or user preference.

In some arrangements, the medial information retrieved at block 605 comprises data indicative of: medical information associated with the patient; medical information associated with one or more further patients; and/or expert medical knowledge.

In embodiments, based on the identified prior actions, the system 103 identifies a further radiologist, and causes the user device 101 to facilitate communication between radiologist and the further radiologist.

In some arrangements, in response to navigation of the identified decision tree S from the root node S1 to the leaf nodes S4a-c, the system 103 prepares a report based on a navigation path from the root node S1 to the one of the plurality of leaf nodes S4a-c.

In the example set forth in FIGS. 7 to 16, an interface or user interface 700 comprising one or more User Interface (UI) portions for presentation of medical information retrieved at blocks 309, 503 and/or 605, or otherwise retrieved. The interface 700 may be provisioned via an application on the user device 101 and/or via an application remote from the user device. The medical information may correspond to one or more patients and may be presented in conjunction with one or more of the functions for use in processing thereof, whereby enabling a radiologist or another healthcare professional in making clinical, administrative and/or management decisions.

In this example, the interface 700 presents data identifying the user, such as a radiologist or another healthcare professional, such as Dr Grossman in UI portion 701. The data identifying the user may, for example, be acquired based on a user and/or access rights verification procedure. User identification may enable the system 103 to apply user-specific customisation, for example, on the basis of monitoring of the prior actions as described above.

In the UI portion 702 the system 103 may cause the interface 700 to present data identifying upcoming appointments, as a work list, for the user. The user may e.g. via interaction with the user interface select a case for review from the cases listed in the UI portion 702 via a man machine interface, such as a mouse or a keypad.

The system 103 may identify a case as recommended case for the user to review in UI portion 703. The recommended case may, for example, correspond to the user's next appointment. In UI portion 704 the system 103 may cause the interface 700 to present relevant medical information relating to the recommended case. For example, the relevant medical information may include identification of clinical stage, patient history, birthday etc. The system 103 may, in response to identifying the recommended case, cause the user device 101 to retrieve the relevant medical information from one or more of the disparate data sources 107 and present at least some of the retrieved medical information via the interface 700 in UI portion 704.

As described above, the system 103 may be coupled to one or more support systems, such as an expert system, a clinical decision support system, a statistical decision support system and/or a population health management system e.g. "Thieme", "Radiopaedia", "Galileo", "Teamplay" for assisting the user in reviewing the medical information. In this example, the interface 700 presents an assistive function in UI portion 705 that selectively uses one or more of the support systems based on a user query. For example, the user may enquire about likely medical conditions based on, for example, symptoms and/or diagnostic procedures carried out in relation to a case, such as the recommended case, and in this case the system may use the expert system to identify likely medical conditions that may be affecting a patient and that may support in analysing the recommended case.

The system causes the interface 700 to present an option for the user to solicit a second opinion from a further radiologist or another healthcare professional in UI portion 706. In response to the user requesting a second opinion, the system 103 may identify a further radiologist or another healthcare professional based on the current node, the state parameter and/or the monitored prior actions in respect of the user as described above.

The system 103 causes the interface 700 to present an option for the user to research a medical topic using online resources in UI portion 707. Online resources may, for example, scientific journals, expert reports, and/or online repositories, such as https://radiopaedia.org/.

Figure 8:
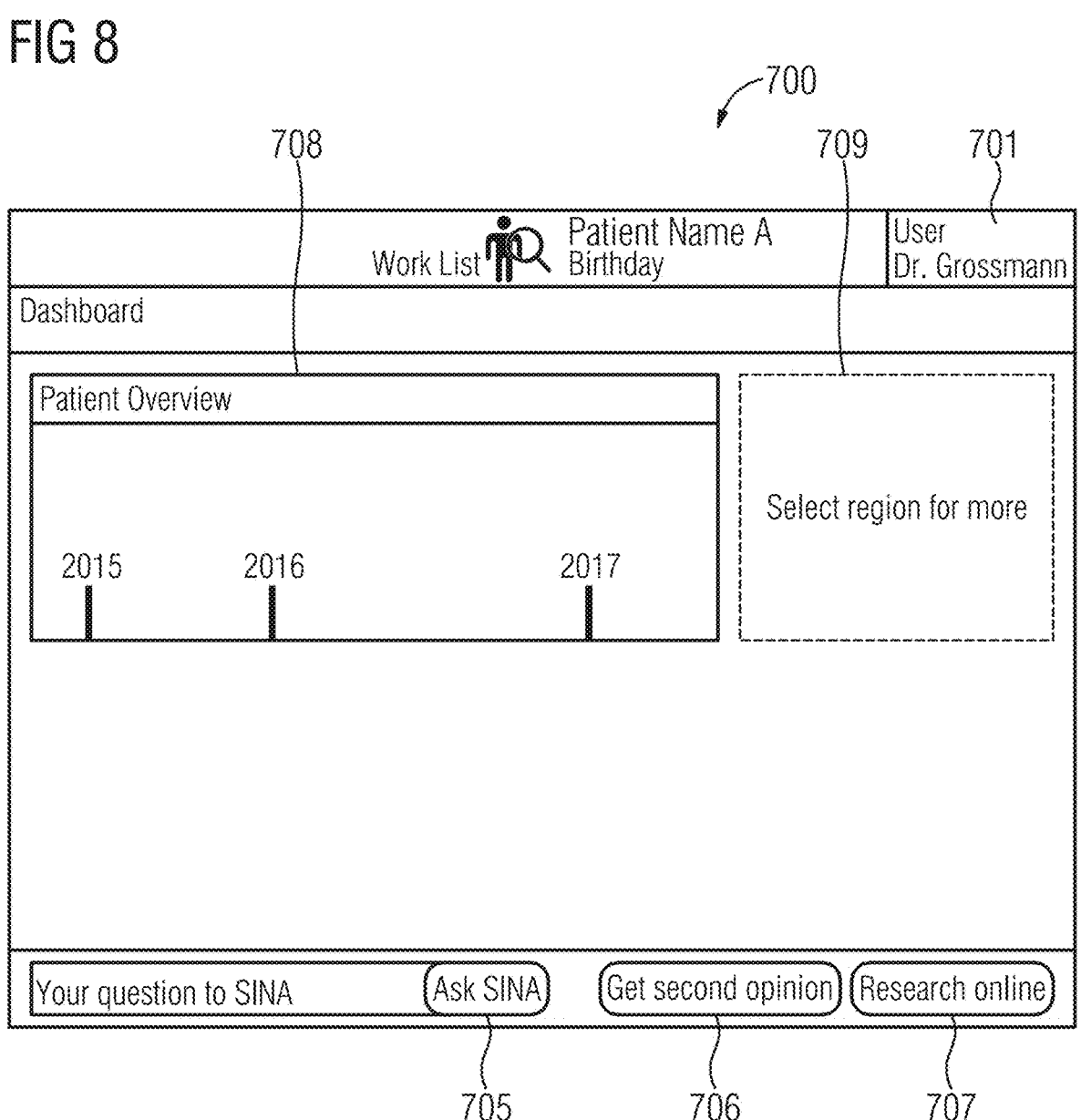
Figure 9:
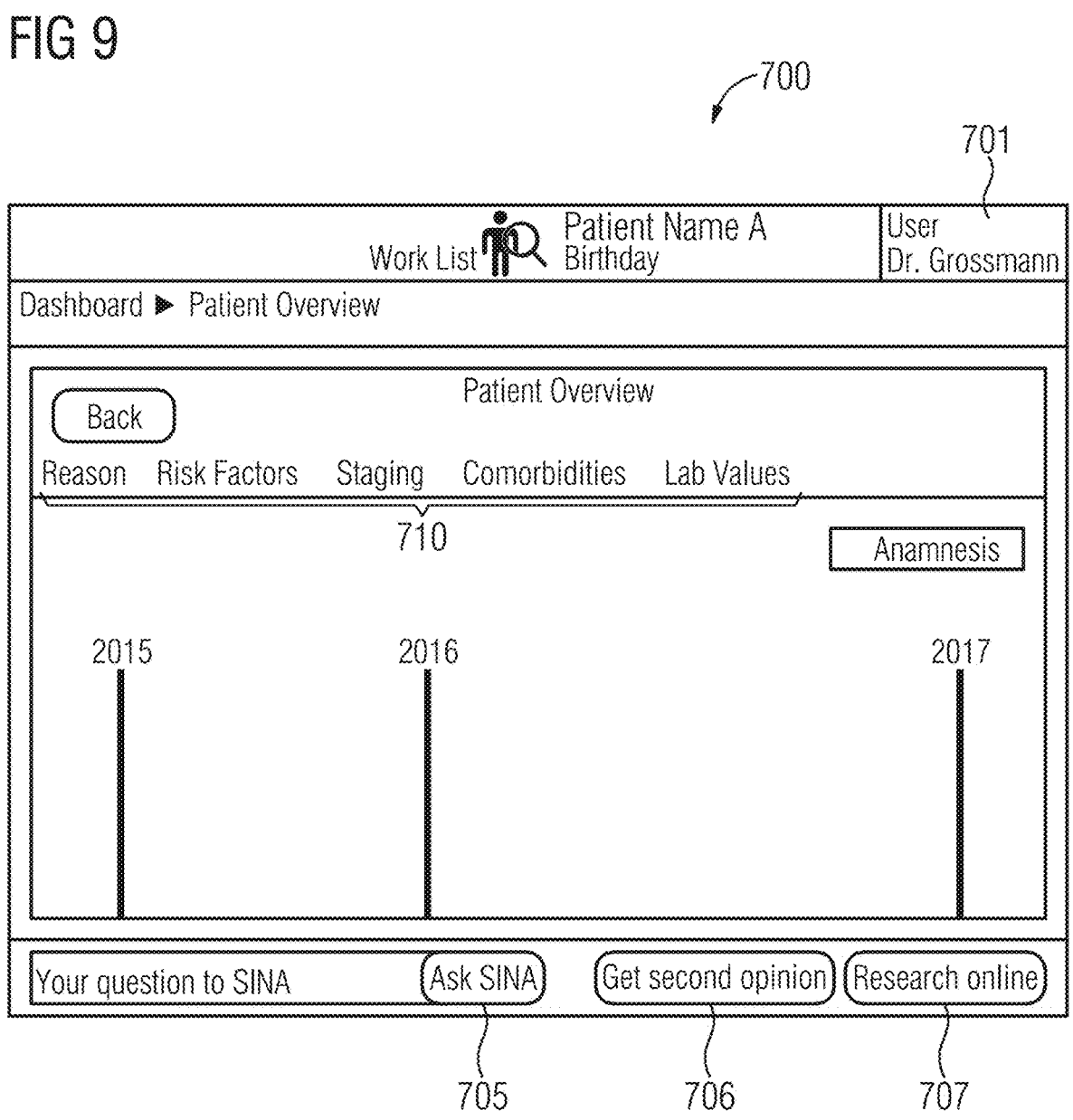
Figure 10:
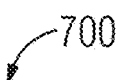
Figure 11:
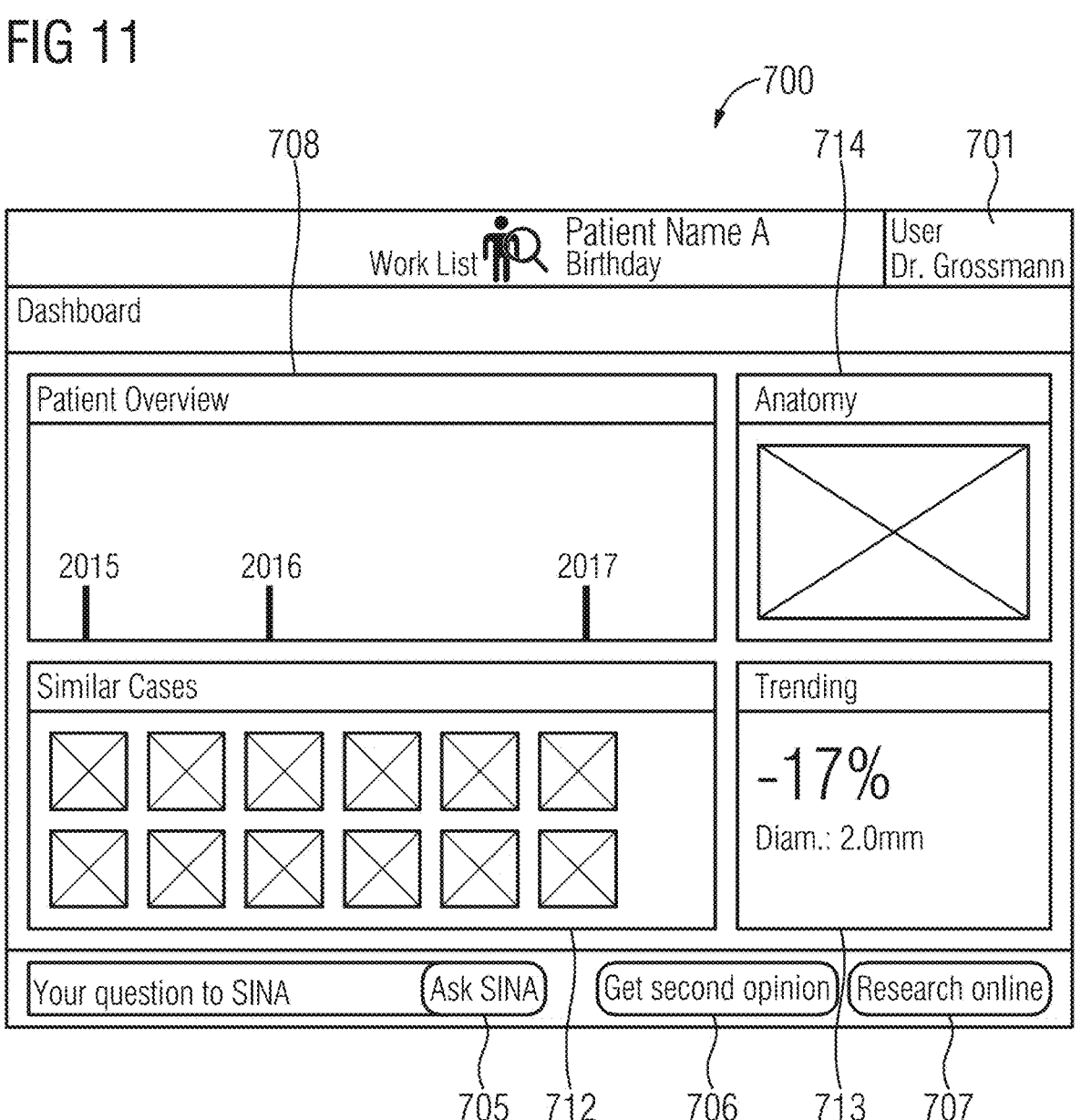

In the example UI set forth in FIG. 8, in response to the user selecting a case for review, the system 103 causes the user device 101 to retrieve relevant medical information from one or more of the data sources 107 based on, for example, a current stage of assessment, which may be identified on the basis of a current node of an identified decision tree and/or the state parameter as described above. The system 103 may generate a timeline with relevant clinical events such as . . . , and cause the interface 700 to present the timeline in UI portion 708. The system 103 may additionally select one or more of graphical elements, such as a recent scan, from the retrieved medical information to give an overview of the case to the user and cause the interface to present it in UI portion 709.

In response to the user selecting the case for a detailed analysis, the system 103 may cause the interface 700 to classify the retrieved medical information from at least one of the plurality of different data sources into different categories. In the example UI set forth in FIG. 9, the retrieved medical information can be classified into various categories, including: reasons; rick factors; staging; comorbidities; and lab values, with a link to each of the categories being displayed in UI portion 710. The category reason may, for example, include data indicative of symptoms experienced and/or patient history. The category risk factors may, for example, include data indicative of patient age and/or lifestyle factors that may affect diagnosis and/or treatment. The category staging may, for example, include data indicative of a stage associated with the identified and/or suspected medical condition. The category comorbidity may, for example, include data indicative of a related or a comorbidity medical condition that the user needs to factor in their assessment. The category lab values may, for example, include data indicative of results from diagnostic and/or therapeutic procedures previously conducted.

In an example UI the interface 700 may display the case under review, e.g. patient name A together with another case of e.g. patient name B for comparison in a corresponding UI portion. The other case may be selected by the system 103 using, for example, one or more of the support systems. Alternatively, in an example UI set forth in FIG. 10 the interface 700 may display for the case under review a follow-up study, for example image data of an affected body region of the patient, i.e. patient name A, and a prior study, i.e. image data of the same affected body region which were acquired some time ago in the UI portion 711 thus enabling comparison of anatomical structures and thereby deducing for example growth/shrinkage of a lesion.

The system may retrieve further relevant medical information using, for example, one or more of the support systems. In the example set forth in FIG. 11, the system may identify similar cases, i.e. cases with similar symptoms and/or conditions, for use in comparison by the user and cause the interface 700 to present the identified similar cases in UI portion 712. The system 103 uses one or more of the support systems to identify trends between various scans carried out over time relating to the case to identify, for example, the trend in growth of the identified lesion and current diameter thereof, and cause the interface 700 to present it in UI portion 713. The system 103 causes the interface 700 to present data indicative of anatomy indicative of the affected organs and/or regions thereof in UI portion 714.

Figure 12:
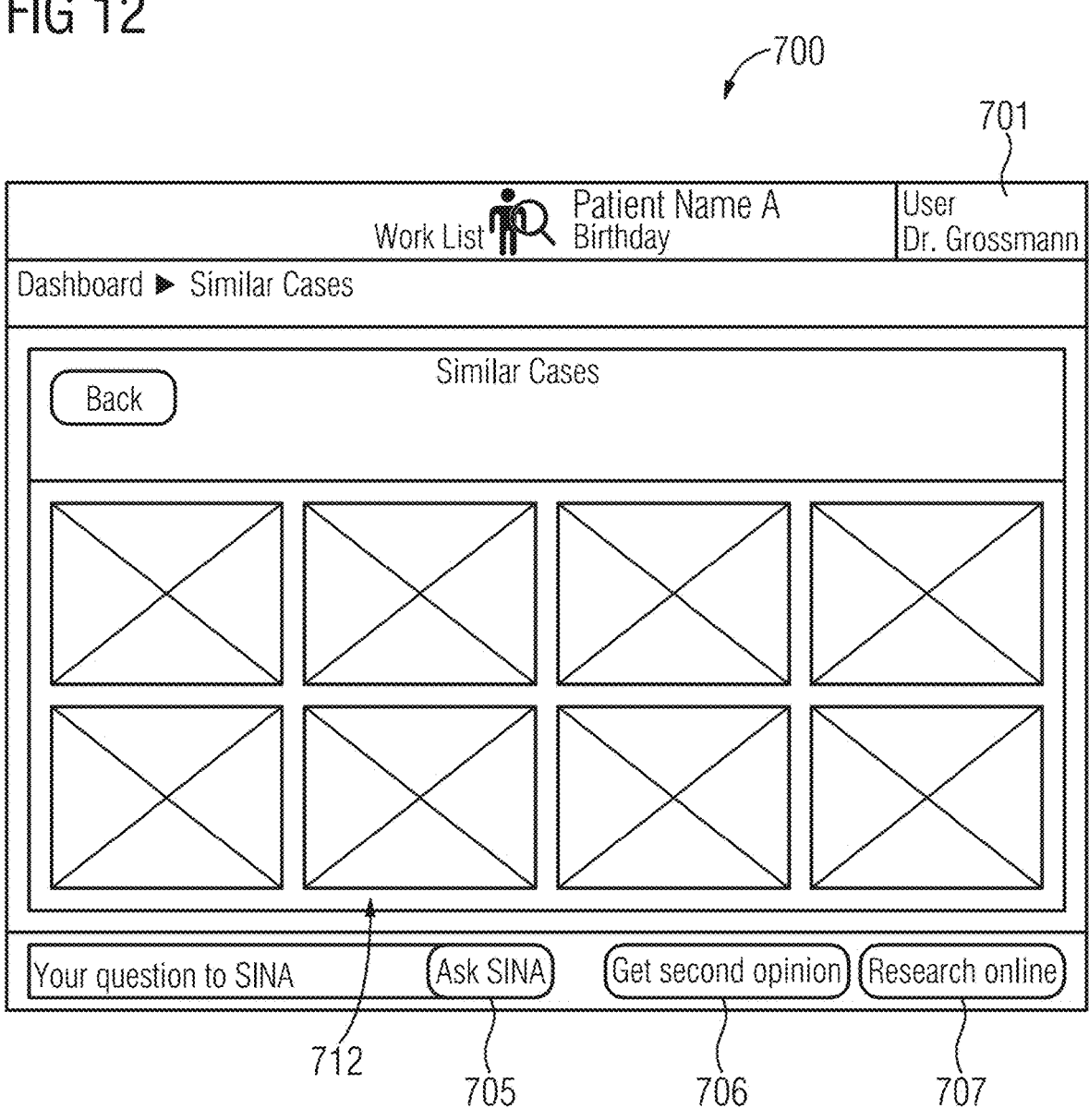
Figure 14:
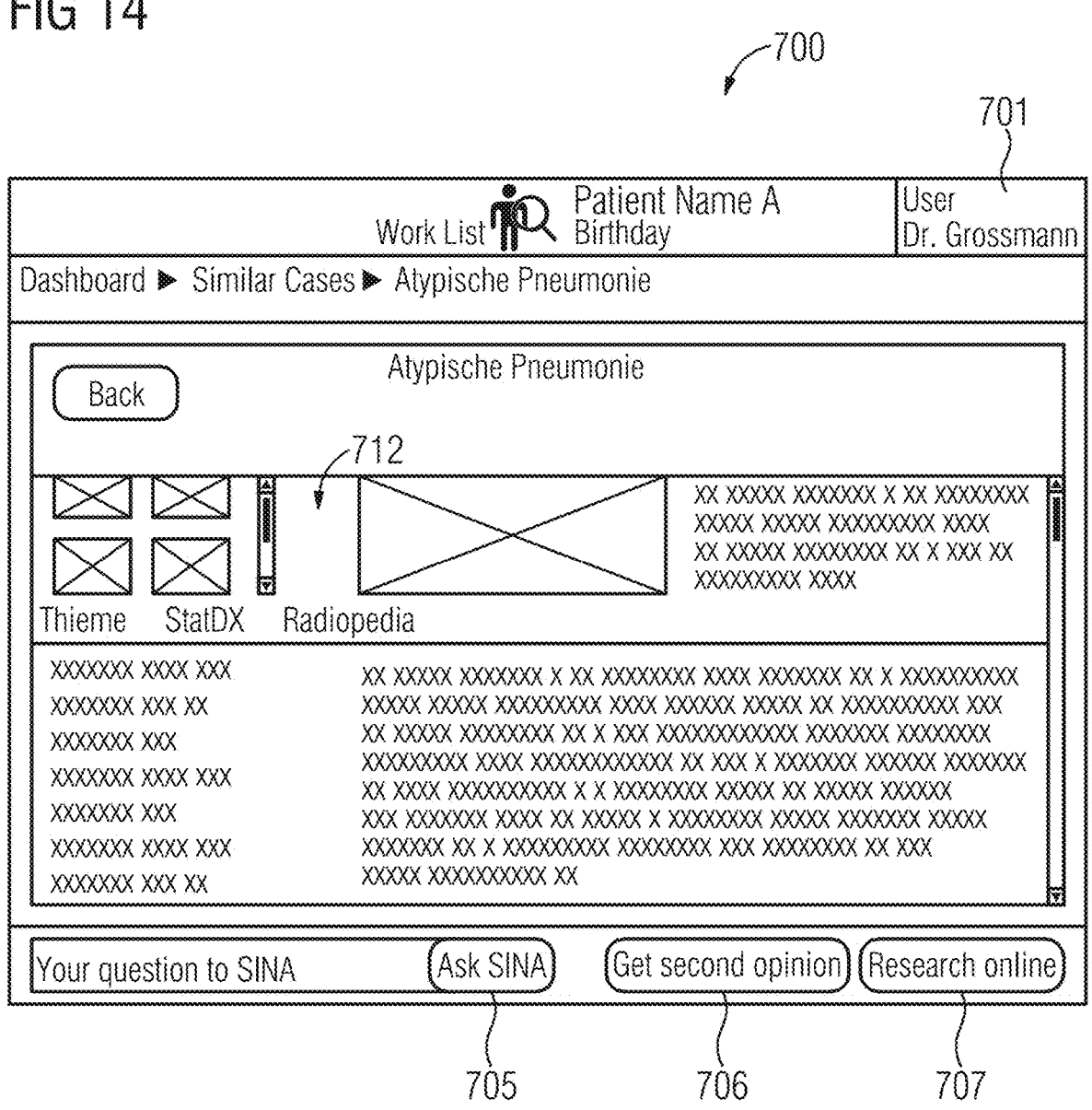

In response to a user input in relation to UI portion 712, the system 103 may cause the interface 700 to display further relevant medical information relating to similar cases, as in the example set forth in FIG. 12.

In response to a user input in relation to UI portion 707, the system 103 retrieves relevant medical information from various online and offline research resources, such as https://radiopaedia.org/, and causes the interface 700 to present it in UI portion 712, as in the example set forth in FIG. 13. The interface 700 automatically updates the presented medical information in response to a user input, such as scrolling, as in the example set forth in FIG. 14.

The system 103, either alone or in conjunction with one or more of the support systems, may generate a list of trending topics from the topics that are of interest to the user, and cause the interface 700 to present it in UI portion 713, as in the example UI set forth in FIG. 15.

Figure 16:
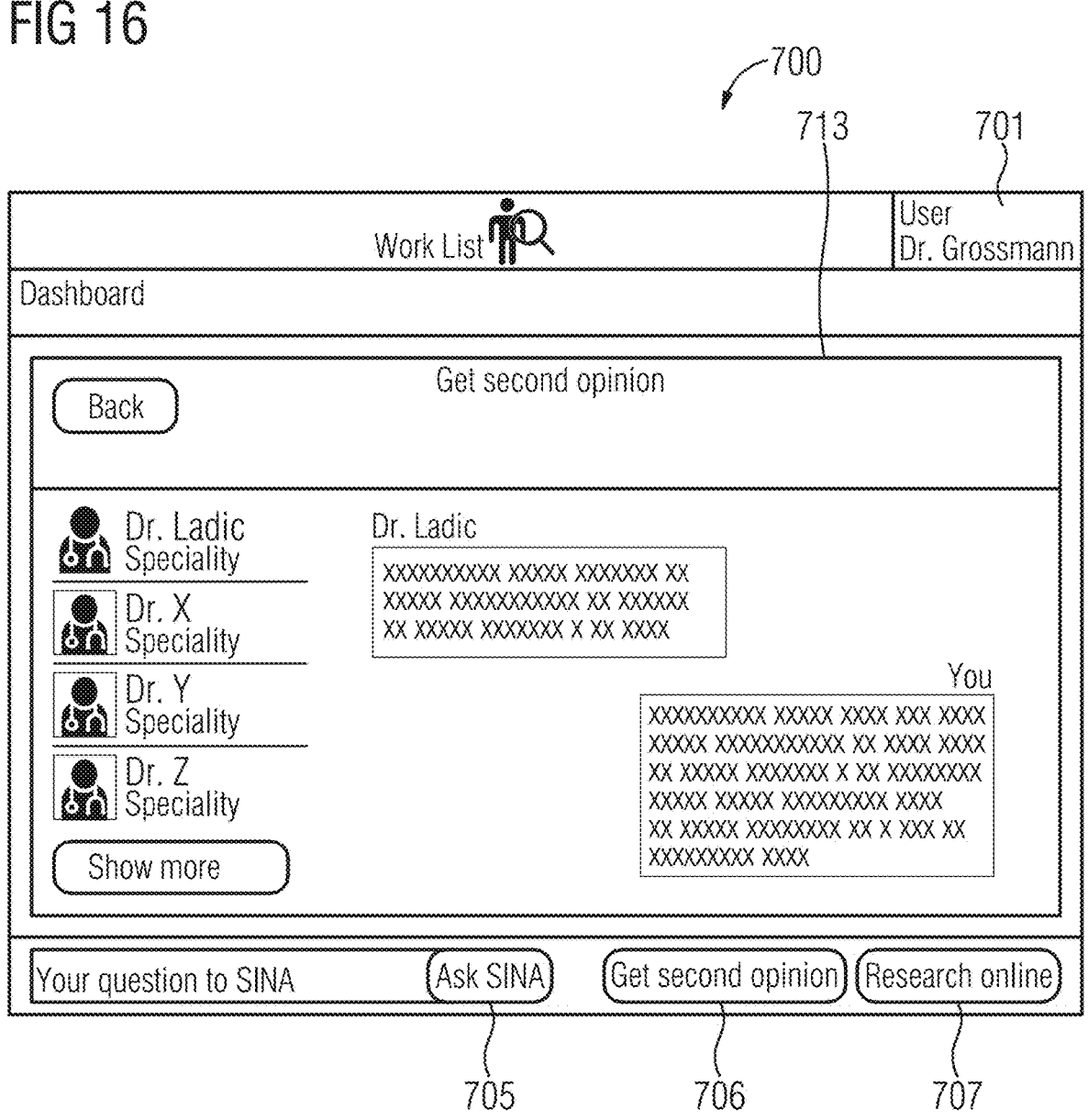

In response to a user input in relation to UI portion 706, the system 103 may identify a further radiologist or another healthcare professional as described above, and cause the interface 700 to facilitate communication between the healthcare professionals via a communications function provisioned in UI portion 713, as in the example set forth in FIG. 16.

Therefore, the framework enables a homogeneous environment in which disparate data sources are integrated based on information required for a current stage in the clinical process. The retrieved information is based on relevant context, and is automatically updated as the analysis advances to a next stage. In addition, presented information is customised in accordance with preferences of radiologists', thereby improving their user experience. In addition, analysis of medical information is controlled by the radiologist, and the system assists the radiologist by providing relevant information.

The above are to be understood as illustrative examples. Further examples are envisaged.

In examples described above, the healthcare network 100 comprises one or more user devices 101, a system 103, a database 105 and one or more data sources 107. In other examples, the healthcare network comprises additional systems.

In examples described above, the system 103 controls operation of a user device configured for use by a radiologist when analysing medical information associated with a patient. In other examples, the system 103 can be configured to control operation of a user device for use by any healthcare professional when analysing medical information associated with a patient.

It is to be understood that any feature described in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the invention, which is defined in the accompanying claims.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

ANNEX

15. A system (103) operable to control operation of a user device (101), the user device (101) being configured for use by a radiologist when analysing medical information associated with a patient, the system (103) comprising at least one processor and at least one memory including computer program code, the at least one memory and the computer program code configured to, with the at least one processor, cause the system (103) at least to perform the steps of:

maintaining, in a database (105), an association between a medical condition and at least one of a plurality of decision trees (S), each decision tree comprising a plurality of nodes organised in a tree structure originating at a root node (S1) and terminating at a plurality of leaf nodes (S4*a-c*) via a plurality of branch nodes (S2*a-c* and S3*a-f*), wherein the root node (S1) and each of the branch nodes have a plurality of outputs, each of the plurality of outputs links a node of the plurality of nodes to a further node of the plurality of nodes and wherein each output causes the system (103) to differently control operation of the user device (101);

in response to receiving medical information associated with the patient, identifying, based on the association, a decision tree from the plurality of decision trees (S); and for the root node (S1) of the identified decision tree (S), performing a process comprising:

causing the user device (101) to retrieve medical information from at least one of a plurality of data sources (107) based on a combination of the root node (S1) and a state parameter, the state parameter being indicative of one of different stages associated with a determination regarding a first output in connection with the root node (S1);

causing at least a part of the retrieved medical information to be displayed on the user device (101); and in response to receiving data indicative of the first output, selecting a first of the plurality of nodes (S2*a-c*).

16. A system (103) according to illustrative embodiment 15, wherein the at least one memory and the computer program code are configured to, with the at least one processor, cause the system (103) to perform the step of:

repeating the process for each of the nodes successive to the first node of the identified decision tree (S), thereby enabling the radiologist to navigate the identified decision tree from the root node (S1) to the leaf nodes (S4*a-c*).

17. A system (103) according to illustrative embodiments 15 or 16, wherein the at least one memory and the computer program code are configured to, with the at least one processor, cause the system (103) to perform the steps of:

based on a combination of the state parameter and data indicative of the retrieved medical information, causing the user device (101) to identify one or more of a plurality of functions usable for processing the retrieved medical information; and causing the user device (101) to provision the identified one or more of the plurality of functions to the radiologist, whereby enabling processing of the retrieved medical information.

18. A system (103) according to any of illustrative embodiments 15 to 17, wherein the at least one memory and the computer program code are configured to, with the at least one processor, cause the system (103) to perform the step of:

in response to receiving an input from the radiologist, causing the user device (101) to present at least a part of the retrieved medical information based on a combination of the input and the state parameter.

19. A system (103) according to any of illustrative embodiments 15 to 18, wherein the at least one memory and the computer program code are configured to, with the at least one processor, cause the system (103) to perform the steps of:

monitoring prior actions of the radiologist when analysing medical information associated with at least some of the different stages; and based on the monitoring, causing at least a part of the retrieved medical information to be displayed on the user device (101).

20. A system (103) according to illustrative embodiment 19, wherein the at least one memory and the computer program code are configured to, with the at least one processor, cause the system (103) to perform the steps of:

based on the monitoring, processing the retrieved medical information; and thereafter causing at least a part of the processed medical information to be displayed on the user device (101).

21. A system (103) according to any of illustrative embodiments 15 to 20, wherein the medical information is retrieved based on:

data indicative of the patient;
data indicative of the radiologist;
data indicative of a medical condition;
data indicative of one or more guidelines;
data indicative of one or more legal regulations;
data acquired on the basis of monitoring of prior actions of the radiologist while navigating at least one of the plurality of decision trees to analyse medical information;

data indicative of a customisation parameter; and/or
data indicative of a user setting.

22. A system (103) according to any of illustrative embodiments 15 to 21, wherein the retrieved medical information comprises data indicative of:

medical information associated with the patient;
medical information associated with one or more further patients; and/or
expert medical knowledge.

23. A system (103) according to any of illustrative embodiments 15 to 22, wherein the at least one memory and the computer program code are configured to, with the at least one processor, cause the system (103) to perform the steps of:

based on a combination of the state parameter and the first node, identifying a further radiologist; and causing the user device (101) to facilitate communication between radiologist and the further radiologist.

24. A system (103) according to any of illustrative embodiments 15 to 23, wherein the at least one memory and the computer program code are configured to, with the at least one processor, cause the system (103) to perform the step of:

in response to navigation of the identified decision tree from the root node (S1) to the leaf nodes (S4*a-c*), preparing a report based on a navigation path from the root node (S1) to the one of the plurality of leaf nodes (S4*a-c*).

25. A system (103) according to any of illustrative embodiments 15 to 24, wherein each of the plurality of outputs correspond to an output from a medical domain.

26. A method of controlling operation of a user device (101), the user device (101) being configured for use by a radiologist when analysing medical information associated with a patient, the method comprising:

maintaining, in a database (105), an association between a medical condition and at least one of a plurality of decision trees (S), each decision tree comprising a plurality of nodes organised in a tree structure originating at a root node (S1) and terminating at a plurality of leaf nodes (S4*a-c*) via a plurality of branch nodes (S2*a-c* and S3*a-f*), wherein the root node (S1) and each of the branch nodes (S2*a-c* and S3*a-f*) have a plurality of outputs, each of the plurality of outputs links a node of the plurality of nodes to a further node of the plurality of nodes and wherein each output causes operation of the user device (101) to be differently controlled;

in response to receiving medical information associated with the patient, identifying, based on the association, a decision tree from the plurality of decision trees (S); and for the root node (S1) of the identified decision tree (S), performing a process comprising:

causing the user device (101) to retrieve medical information from at least one of a plurality of data sources (107) based on a combination of the root node (S1) and a state parameter, the state parameter being indicative of one of different stages associated with a determination regarding a first output in connection with the root node (S1);

causing at least a part of the retrieved medical information to be displayed on the user device (101); and in response to receiving data indicative of the first output, selecting a first of the plurality of nodes (S2*a-c*).

27. A computer program comprising a set of instructions, which, when executed by a computerised device, cause the computerised device to perform a method of controlling operation of a user device (101), the user device (101) being configured for use by a radiologist when analysing medical information associated with a patient, the method comprising, at the computerised device:

maintaining, in a database (105), an association between a medical condition and at least one of a plurality of decision trees (S), each decision tree comprising a plurality of nodes organised in a tree structure originating at a root node (S1) and terminating at a plurality of leaf nodes (S4a-c) via a plurality of branch nodes (S2a-c and S3a-f), wherein the root node (S1) and each of the branch nodes (S2a-c and S3a-f) have a plurality of outputs, each of the plurality of outputs links a node of the plurality of nodes to a further node of the plurality of nodes and wherein each output causes operation of the user device (101) to be differently controlled;

in response to receiving medical information associated with the patient, identifying, based on the association, a decision tree from the plurality of decision trees (S); and for the root node (S1) of the identified decision tree (S), performing a process comprising:

causing the user device (101) to retrieve medical information from at least one of a plurality of data sources (107) based on a combination of the root node (S1) and a state parameter, the state parameter being indicative of one of different stages associated with a determination regarding a first output in connection with the root node (S1);

causing at least a part of the retrieved medical information to be displayed on the user device (101); and in response to receiving data indicative of the first output, selecting a first of the plurality of nodes (S2a-c).

28. A system (103) operable to control operation of a user device (101), the user device (101) being configured for use by a radiologist when analysing medical information associated with a patient, the system (103) comprising at least one processor and at least one memory including computer program code, the at least one memory and the computer program code configured to, with the at least one processor, cause the system (103) at least to perform the steps of:

maintaining, in a database (105), an association between a medical condition and at least one of a plurality of decision trees (S), each decision tree comprising a plurality of nodes organised in a tree structure originating at a root node (S1) and terminating at a plurality of leaf nodes (S4a-c) via a plurality of branch nodes (S2a-c and S3a-f), wherein the root node (S1) and each of the branch nodes have a plurality of outputs, each of the plurality of outputs links a node of the plurality of nodes to a further node of the plurality of nodes and wherein each output causes the system (103) to differently control operation of the user device;

identifying a plurality of prior actions performed by the radiologist while navigating at least one of the plurality of decision trees to analyse medical information;

in response to receiving medical information associated with the patient, identifying, based on the association, a decision tree from the plurality of decision trees (S); and for the root node (S1) of the identified decision tree (S), performing a process comprising:

causing the user device (101) to retrieve medical information from at least one of a plurality of data sources (107) based on the root node (S1) and to process the retrieved medical information based on the identified prior actions; and causing at least a part of the processed medical information to be displayed on the user device (101).

29. A system (103) according to illustrative embodiment 28, wherein the at least one memory and the computer program code are configured to, with the at least one processor, cause the system (103) to perform the step of:

in response to receiving data indicative of a first of a plurality of outputs in connection with the root node (S1), selecting a first of the plurality of nodes (S2a-c).

30. A system (103) according to illustrative embodiment 29, wherein the at least one memory and the computer program code are configured to, with the at least one processor, cause the system (103) to perform the step of:

repeating the process for each of the nodes successive to the first node of the identified decision tree, thereby enabling the radiologist to navigate the identified decision tree from the root node (S1) to the leaf nodes (S4a-c).

31. A system (103) according to illustrative embodiments 29 or 30, wherein the at least one memory and the computer program code are configured to, with the at least one processor, cause the system (103) to perform the steps of:

maintaining a state parameter indicative of a stage associated with a determination of a first output in connection with the root node (S1); and causing the user device (101) to present at least a part of the retrieved medical information based on the state parameter.

32. A system (103) according to any of illustrative embodiments 28 to 31, wherein the at least one memory and the computer program code are configured to, with the at least one processor, cause the system (103) to perform the step of:

based on a combination of the root node (S1) and data indicative of the identified prior actions, causing the user device (101) to identify one or more of a plurality of functions usable for processing the retrieved medical information.

33. A system (103) according to illustrative embodiment 32, wherein the at least one memory and the computer program code are configured to, with the at least one processor, cause the system (103) to perform the step of:

using at least one of the one or more of a plurality of functions for the processing of the retrieved medical information.

34. A system (103) according to illustrative embodiment 32, wherein the at least one memory and the computer program code are configured to, with the at least one processor, cause the system (103) to perform the step of:

causing the user device (101) to provision the identified one or more of the plurality of functions to the radiologist, whereby enabling the radiologist to analyse the processed medical information.

35. A system (103) according to any of illustrative embodiments 28 to 34, wherein the at least one memory and the computer program code are configured to, with the at least one processor, cause the system (103) to perform the step of:

in response to receiving an input from the radiologist, causing the user device (101) to present at least a part of the retrieved medical information based on a combination of the input and the identified prior actions.

36. A system (103) according to any of illustrative embodiments 28 to 35, wherein the at least one memory and the computer program code are configured to, with the at least one processor, cause the system (103) to perform the step of:
    causing the user device (101) to process the retrieved medical information based on:
    data associated with the patient;
    data associated with another patient;
    data indicative of the radiologist;
    data indicative of a medical condition;
    data indicative of one or more guidelines;
    data indicative of one or more legal regulations;
    data indicative of a customisation parameter; and/or
    data indicative of a user setting.

37. A system (103) according to any of illustrative embodiments 28 to 35, wherein the medical information is retrieved based on:
    data indicative of the patient;
    data indicative of the radiologist;
    data indicative of a medical condition;
    data indicative of one or more guidelines;
    data indicative of one or more legal regulations;
    data indicative of a customisation parameter; and/or
    data indicative of a user setting.

38. A system (103) according to any of illustrative embodiments 28 to 37, wherein the retrieved medical information comprises data indicative of:
    medical information associated with the patient;
    medical information associated with one or more further patients; and/or
    expert medical knowledge.

39. A system (103) according to any of illustrative embodiments 28 to 38, wherein the at least one memory and the computer program code are configured to, with the at least one processor, cause the system (103) to perform the steps of:
    based on the identified prior actions, identifying a further radiologist; and
    causing the user device (101) to facilitate communication between radiologist and the further radiologist.

40. A system (103) according to any of illustrative embodiments 28 to 39, wherein the at least one memory and the computer program code are configured to, with the at least one processor, cause the system (103) to perform the step of:
    in response to navigation of the identified decision tree from the root node (S1) to the leaf nodes (S4a-c), preparing a report based on a navigation path from the root node (S1) to the one of the plurality of leaf nodes (S4a-c).

41. A system (103) according to any of illustrative embodiments 28 to 40, wherein each of the plurality of outputs correspond to an output from a medical domain.

42. A method of controlling operation of a user device, the user device (101) being configured for use by a radiologist when analysing medical information associated with a patient, the method comprising:
    maintaining, in a database (105), an association between a medical condition and at least one of a plurality of decision trees (S), each decision tree comprising a plurality of nodes organised in a tree structure originating at a root node (S1) and terminating at a plurality of leaf nodes (S4a-c) via a plurality of branch nodes (S2a-c and S3a-f), wherein the root node (S1) and each of the branch nodes (S2a-c and S3a-f) have a plurality of outputs, each of the plurality of outputs links a node of the plurality of nodes to a further node of the plurality of nodes and wherein each output causes operation of the user device (101) to be differently controlled;
identifying a plurality of prior actions performed by the radiologist while navigating at least one of the plurality of decision trees to analyse medical information;
in response to receiving medical information associated with the patient, identifying, based on the association, a decision tree from the plurality of decision trees (S); and
for the root node (S1) of the identified decision tree (S), performing a process comprising:
    causing the user device (101) to retrieve medical information from at least one of a plurality of data sources (107) based on the root node (S1) and to process the retrieved medical information based on the identified prior actions; and
    causing at least a part of the processed medical information to be displayed on the user device (101).

43. A computer program comprising a set of instructions, which, when executed by a computerised device, cause the computerised device to perform a method of controlling operation of a user device (101), the user device (101) being configured for use by a radiologist when analysing medical information associated with a patient, the method comprising, at the computerised device:
    maintaining, in a database (105), an association between a medical condition and at least one of a plurality of decision trees (S), each decision tree comprising a plurality of nodes organised in a tree structure originating at a root node (S1) and terminating at a plurality of leaf nodes (S4a-c) via a plurality of branch nodes (S2a-c and S3a-f), wherein the root node (S1) and each of the branch nodes (S2a-c and S3a-f) have a plurality of outputs, each of the plurality of outputs links a node of the plurality of nodes to a further node of the plurality of nodes and wherein each output causes operation of the user device (101) to be differently controlled;
    identifying a plurality of prior actions performed by the radiologist while navigating at least one of the plurality of decision trees to analyse medical information;
    in response to receiving medical information associated with the patient, identifying, based on the association, a decision tree from the plurality of decision trees (S); and for the root node (S1) of the identified decision tree (S), performing a process comprising:
    causing the user device (101) to retrieve medical information from at least one of a plurality of data sources (107) based on the root node (S1) and to process the retrieved medical information based on the identified prior actions; and
    causing at least a part of the processed medical information to be displayed on the user device (101).

What is claimed is:
1. A system configured to control operation of a user device, the user device being configured for use by a radiologist when analysing medical information associated with a current patient, the system comprising:
    at least one processor, the at least one processor configured to execute machine-readable instructions, that, when executed by the at least one processor, cause the system at least to
    provide at least one machine learning system that organizes actions at various diagnostic stages, each of the at least one machine learning systems causing the system to control operation of the user device differently, identify, in response to receiving first medical information associated with the current patient, an identified machine learning system from the at least one machine learning systems, retrieve second medical information, different from the first medical information, from at least one of a plurality of disparate data sources based at least on the identified machine learning system, and control operation of the user device based on the at least one of the plurality of disparate data sources from which the second medical information is retrieved by causing the user device to display one or more of a plurality of image processing functions usable for processing the retrieved second medical information.

2. The system of claim 1, wherein the at least one processor is configured to execute the machine-readable instructions, that when executed by the at least one processor, cause the system to:

maintain a state parameter indicative of a diagnostic stage; and cause the user device to present at least a part of the retrieved second medical information based on the state parameter.

3. The system of claim 2, wherein the at least one processor is configured to execute the machine-readable instructions that, when executed by the at least one processor, cause the system to:

cause the user device, in response to receiving an input from the radiologist, to present at least a part of the retrieved second medical information, the part based on a combination of the input and the state parameter.

4. The system of claim 1, wherein the medical information is retrieved based on at least one of:

data indicative of the current patient;

data indicative of the radiologist;

data indicative of a medical condition;

data indicative of one or more guidelines;

data indicative of one or more legal regulations;

data indicative of a customisation parameter; and data indicative of a user setting.

5. The system of claim 1, wherein the retrieved second medical information comprises data indicative of at least one of:

medical information associated with the current patient;

medical information associated with one or more further patients; and expert medical knowledge.

6. The system of claim 1, wherein the at least one processor is configured to execute the machine-readable instructions that, when executed by the at least one processor, cause the system to:

identify a further radiologist based at least on the identified machine learning system; and cause the user device to facilitate communication between the radiologist and the further radiologist.

7. The system of claim 1, wherein the at least one processor is configured to execute the machine-readable instructions that, when executed by the at least one processor, cause the system to:

process at least a part of the retrieved second medical information based at least on a parameter; and thereafter cause at least a part of the second medical information processed to be displayed on the user device.

8. The system of claim 7, wherein the parameter comprises at least one of:

data acquired based upon monitoring of prior actions of the radiologist while navigating the identified machine learning system; and data indicative of a protocol associated with a medical condition.

9. The system of claim 1, wherein the at least one processor is configured to execute the machine-readable instructions that, when executed by the at least one processor, cause the system to:

prepare a report, in response to using the identified machine learning system, based on a navigation path through the identified machine learning system.

10. The system of claim 1, wherein each of the plurality of disparate data sources correspond to an output from a medical domain.

11. A user device configured for use by a radiologist when analysing medical information associated with a current patient, the user device comprising:

at least one processor configured to execute machine-readable instructions that, when executed by the processor, cause the user device to provision at least one machine learning system that organizes actions at various diagnostic stages, each of the at least one machine learning systems controlling operation of the user device differently, identify, in response to receiving first medical information associated with the current patient, an identified machine learning system from the at least one machine learning system, retrieve second medical information, different from the first medical information, from at least one of a plurality of disparate data sources based on learned preferences of the radiologist and on the identified machine learning system, and based on the at least one of the plurality of disparate data sources from which the second medical information is retrieved, control a display of one or more of a plurality of image processing functions usable for processing the retrieved second medical information.

12. The system of claim 2, wherein the at least one processor is configured to execute the machine-readable instructions that, when executed by the at least one processor, cause the system to:

maintain the state parameter indicative of a stage of treatment of the current patient; and cause the user device to present at least a part of the retrieved second medical information based on the state parameter.

13. The system of claim 12, wherein the at least one processor is configured to execute the machine-readable instructions that, when executed by the at least one processor, cause the system to:

cause the user device, in response to receiving an input from the radiologist, to present at least a part of the retrieved second medical information based on a combination of the input and the state parameter.

14. The system of claim 2, wherein the at least one processor is configured to execute the machine-readable instructions that, when executed by the at least one processor, cause the system to:

process at least a part of the retrieved second medical information based at least on a parameter; and thereafter cause at least a part of the second medical information processed to be displayed on the user device.

15. The system of claim 14, wherein the parameter comprises at least one of:

data acquired based upon monitoring of prior actions of the radiologist while navigating the identified machine learning system to analyse medical information; and data indicative of a protocol associated with a medical condition.

16. The system of claim 2, wherein the at least one processor is configured to execute the machine-readable instructions that, when executed by the at least one processor, cause the system to:

prepare a report, in response to navigation of the identified machine learning system, based on a navigation path along the identified machine learning system.

17. The system of claim 1, wherein the plurality of disparate data sources include at least one of:

a picture archiving and communication system (PACS), an electronic medical records (EMR) source, an emergency care summary (ECS) source, a key information summary (KIS) source, an electronic patient record (EPR) source, and a personal health record (PHR) source.

18. The system of claim 1, wherein the image processing functions includes one or more of a first function to measure one or more of a size, a volume, or a diameter of a lesion, a second function to measure a distance of the lesion to a predefined landmark or predefined organ, a third function to color map or zoom, or a fourth function to identify differences between medical images.

19. The system of claim 1, wherein the at least one processor is configured to execute the machine-readable instructions that, when executed by the at least one processor, cause the system to:

cause the user device to retrieve medical information from at least one of the plurality of disparate data sources additionally based on learned preferences of the radiologist.

20. The system of claim 1, wherein the at least one processor is configured to execute the machine-readable instructions that, when executed by the at least one processor, cause the system to:

cause the user device to process the retrieved second medical information based on at least the identified machine learning system; and cause the user device to display a result of processing the retrieved second medical information based on at least the identified machine learning system.

21. The system of claim 1, wherein the at least one processor is configured to execute the machine-readable instructions that, when executed by the at least one processor, cause the system to:

retrieve the one or more of the plurality of image processing functions based on the identified machine learning system and/or the retrieved second medical information.

22. The system of claim 1, wherein the first medical information includes at least one of medical images, image data sets, or medical image studies, and the second medical information includes at least one of laboratory test results of the current patient, electronic health records of the current patient, patient/disease registries indicative of data relating to chronic conditions, clinical trials data, administrative data, regulatory data, research and development data, or legal data.

23. The system of claim 22, wherein the at least one machine learning system includes a decision tree.

* * * * *